(12) United States Patent
Kristiansen et al.

(10) Patent No.: US 8,512,681 B2
(45) Date of Patent: Aug. 20, 2013

(54) CHEWING GUM POSSESSING TOOTH CLEANING EFFECT AND A TEETH CLEANING METHOD

(75) Inventors: Tove Nordestgaard Kristiansen, Jelling (DK); Lars Gyldenvang, Grenaa (DK); Rikke Mikkelsen, Vejle (DK)

(73) Assignee: GUMLINK A/S, Vejle (DK)

( * ) Notice: Subject to any disclaimer, the term of this patent is extended or adjusted under 35 U.S.C. 154(b) by 0 days.

(21) Appl. No.: 13/117,197

(22) Filed: May 27, 2011

(65) Prior Publication Data

US 2011/0229539 A1   Sep. 22, 2011

Related U.S. Application Data

(62) Division of application No. 11/340,797, filed on Jan. 27, 2006, now abandoned.

(30) Foreign Application Priority Data

Jan. 28, 2005 (EP) .................................. 05388006
Jan. 28, 2005 (EP) .................................. 05388007

(51) Int. Cl.
*A61K 9/68* (2006.01)
*A61K 8/02* (2006.01)

(52) U.S. Cl.
USPC ............................................. 424/48; 424/401

(58) Field of Classification Search
None
See application file for complete search history.

(56) References Cited

U.S. PATENT DOCUMENTS

| | | | |
|---|---|---|---|
| 3,070,510 A | 12/1962 | Cooley et al. | |
| 3,429,963 A | 2/1969 | Shedlovsky | |
| 3,506,720 A | 4/1970 | Binder et al. | |
| 3,590,120 A | 6/1971 | Muhler | |
| 3,678,154 A | 7/1972 | Widder et al. | |
| 3,737,533 A | 6/1973 | Moon et al. | |
| 3,862,307 A | 1/1975 | DiGiulio | |
| 3,988,443 A | 10/1976 | Plöger et al. | |
| 4,304,766 A | 12/1981 | Chang | |
| 4,340,583 A | 7/1982 | Wason | |
| 4,661,341 A | 4/1987 | Benedict et al. | |
| 4,846,650 A | 7/1989 | Benedict et al. | |
| 4,877,603 A | 10/1989 | Degenhardt et al. | |
| 4,980,153 A | 12/1990 | Jackson | |
| 4,994,262 A | 2/1991 | Charbonneau et al. | |
| 5,380,350 A | 1/1995 | Fersch | |
| 5,380,530 A | 1/1995 | Hill | |
| 5,693,334 A | 12/1997 | Miskewitz | |
| 5,824,291 A | 10/1998 | Howard | |
| 5,885,630 A | 3/1999 | Zurawski et al. | |
| 6,235,318 B1 | 5/2001 | Lombardy, Jr. et al. | |
| 6,365,130 B1 | 4/2002 | Barry et al. | |
| 6,814,958 B1 | 11/2004 | Sekimoto | |
| 2001/0012636 A1 | 8/2001 | Azar | |
| 2001/0047009 A1 | 11/2001 | Barabolak | |
| 2003/0158111 A1 * | 8/2003 | Bar-Or ............................ 514/12 |
| 2004/0115247 A1 | 6/2004 | Melman | |
| 2005/0042184 A1 | 2/2005 | Colle | |

FOREIGN PATENT DOCUMENTS

| | | |
|---|---|---|
| EP | 0 251 591 | 1/1988 |
| EP | 0 251 591 | 1/1998 |
| EP | 1 072 254 | 1/2001 |
| GB | 490384 | 8/1938 |
| WO | 99/14424 | 7/1994 |
| WO | 95/25436 | 9/1995 |
| WO | 99/15435 | 4/1999 |
| WO | 00/42861 | 7/2000 |
| WO | 01/14875 | 3/2001 |
| WO | 02/074099 | 9/2002 |
| WO | 03/039503 | 5/2003 |
| WO | 2004068965 | 8/2004 |
| WO | WO 2004068965 | * 8/2004 |

OTHER PUBLICATIONS (Townsend Letter for doctors and Patients, Aug.-Sep. 2004 by Alan R. Gaby).*
Gaby et al., "Xylitol Chewing Gum for Prevention of Caries", Townsend Letter for Doctors and Patients, pp. 1-3 (2004).
Merck Index No. 9573.
Merck Index No. 2095.
Merck Index No. 223.
Merck Index No. 1072.
Merck Index No. 8299.
Merck Index No. 3414.
Merck Index 2025—Cevadine.
Merck Index—Hexocylclium Methyl Sulfate.
Merck Index Samandarine.

* cited by examiner

*Primary Examiner* — Brian Gulledge
*Assistant Examiner* — Snigdha Maewall
(74) *Attorney, Agent, or Firm* — Sughrue Mion, PLLC

(57) ABSTRACT

The invention relates to a chewing gum possessing tooth cleaning effects, excluding the tooth brush abrasive effect, which chewing gum when chewed on a daily basis as a tooth cleaning agent is capable of replacing the daily tooth brushing, whereby abrasive cleaning damages on teeth side surfaces and gingiva are avoided.

24 Claims, 1 Drawing Sheet

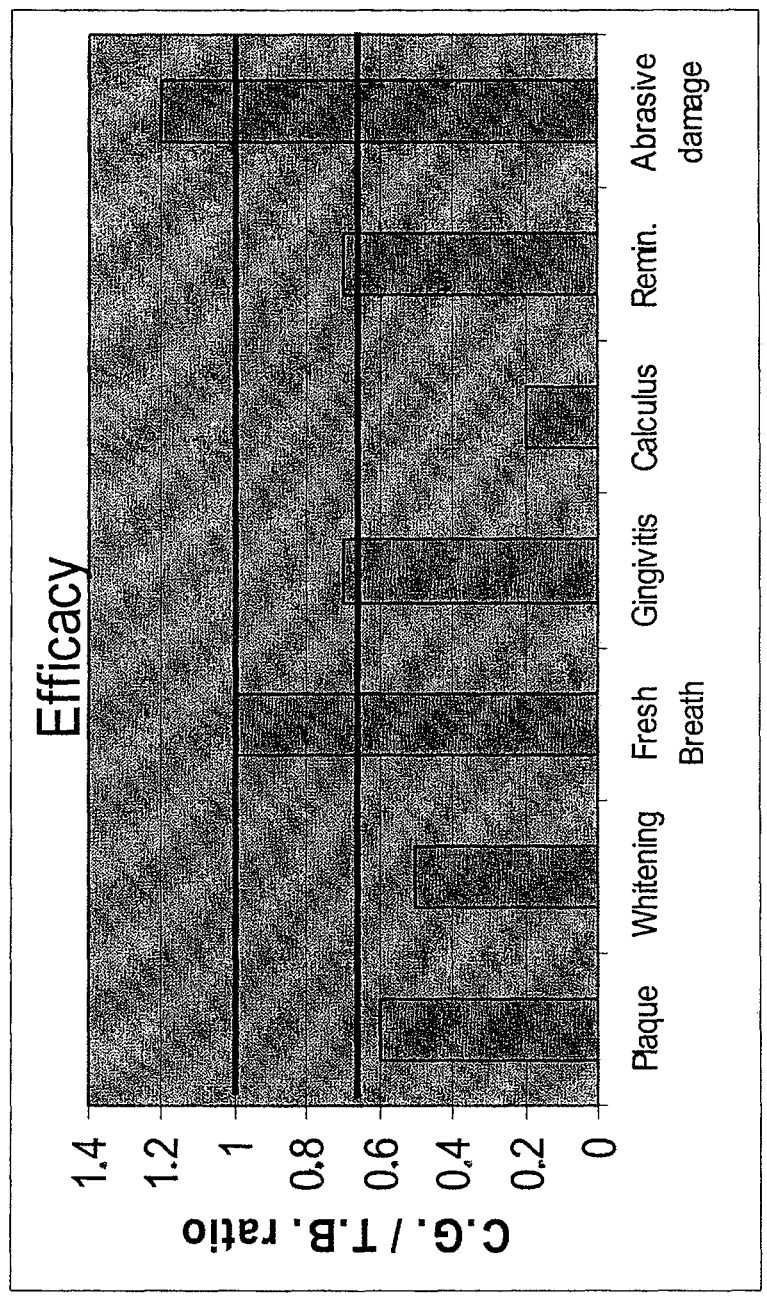

CHEWING GUM POSSESSING TOOTH CLEANING EFFECT AND A TEETH CLEANING METHOD

CROSS-REFERENCE TO RELATED APPLICATIONS

The present application is a Divisional of U.S. Application No. 11/340,797, filed Jan. 27, 2006; which claims benefit of priority from European Patent Application No. 05388006.8, filed Jan. 28, 2005, and from European Patent Application No. 05388007.6, filed Jan. 28, 2005; the disclosure of each of which is incorporated herein by reference.

STATEMENT REGARDING FEDERALLY SPONSORED RESEARCH OR DEVELOPMENT

Not Applicable

REFERENCE TO A MICROFICHE APPENDIX

Not Applicable

BACKGROUND OF THE INVENTION

The present invention relates to a chewing gum possessing tooth cleaning effects.

Chewing gum suitable for temporary tooth cleaning is known. Such chewing gum is e.g. disclosed in the U.S. Pat. Nos. 5,380,530; 5,693,334; 6,365,130; and US patent publication No. 2004/0115247 A1. These types of chewing gum have only been capable to demonstrate a limited capacity for tooth cleaning for single day use or at the most for use during a few days when a toothbrush is accidentally not available. After such a day a thorough cleaning with toothbrush and toothpaste has been required. These types of chewing gum with tooth cleaning effect may be used as a supplement to daily cleaning with a toothbrush and toothpaste.

Brushing of teeth with a toothbrush is, however, rather rough on the teeth and especially on the gingiva and will eventually lead to abrasive damage on the treated teeth or on the gingiva.

For several decades professionals and also in general adults and particularly parents have been convinced that the only suitable method of properly cleaning teeth is daily use of a toothbrush and toothpaste.

From time to time most people experience that a toothbrush is unavailable and then have to resort to using other means, such as a chewing gum or lozenges or using gargle, in order to at least obtain a sensation of fresh breath. But in doing so they are clearly aware that such use does not account to proper tooth cleaning.

People continue to brush teeth daily even when they experience brushing damages or abrasive damages. They will sometimes change to use toothbrushes having softer brushes and many use electrical toothbrushes in order to obtain more favourable brush movements over the teeth and gingiva surfaces, but they do not dispense with tooth brushing as such.

BRIEF SUMMARY OF THE INVENTION

An object of the present invention is to provide a safe and easy-to-use dental care product for daily use.

Consequently, the present invention relates to a chewing gum possessing tooth brush cleaning effects, excluding the tooth brush abrasive effect, which chewing gum when chewed on a daily basis functions to replace daily tooth brushing, whereby abrasive cleaning damages on teeth side surfaces and gingiva are avoided.

Evidently, the present invention provides a surprising solution to the existing problem of how to clean teeth and at the same time avoid the highly undesired effect of causing abrasive damages on teeth side surfaces and gingiva. According to the present invention daily tooth brushing is replaced by chewing of chewing gum making teeth cleaning with toothbrush and toothpaste superfluous for extended periods of time, such as months or years. As a consequence the highly undesired effect of abrasive damages caused by toothbrush and toothpaste on the teeth and gingival is eliminated and the tooth cleaning thus made safe, while the cleaning quality of the teeth in general substantially corresponds to or is better than the cleaning quality obtained by toothbrush and toothpaste.

The toothbrush abrasive effect is in the present context understood as the brushing effect causing abrasive damage on gingiva and the teeth side surfaces. The mechanism involved in development of these damages is understood in the following manner. During the brushing of teeth with a toothbrush, the toothbrush bristles push against the gingiva and cause exposure of the innermost portion of the tooth side surface. This portion of the tooth side surface normally lies well protected behind gingival tissue. This portion is weak in a mechanical sense because the enamel is thin or even missing in this portion. By the brushing the toothbrush bristles act abrading on this weak portion of the tooth side surface. The bristles also penetrate in between the gingiva and said weak portion of the tooth and can cause abrasive damage on the gingival tissue so that gingiva over time is worn down with the result that said weak portion is permanently exposed. With respect to the outer portion of the tooth the enamel is here so thick and strong that the toothbrush cannot in the outer portion really act with an abrasive effect in the sense of the present description.

The chewing gum according to the present invention provides surprisingly a dental care product that can be used on a daily basis with teeth cleaning properties making teeth cleaning with toothbrush and toothpaste superfluous. Cleaning of teeth by daily chewing of the chewing gum makes it possible to avoid the abrasive damages on teeth and gingiva because the toothbrush is no longer required.

The daily chewing of the chewing gum according to the invention is much easier and more convenient in use than the conventional toothbrush with toothpaste. This is in particular advantageous in case of children and disabled persons to whom handling of a toothbrush can be extremely difficult, which fact may very easily lead to the effect that the teeth cleaning becomes ineffective. Moreover, the daily chewing agent according to the invention can be used anywhere at any desired time, as there is no need for access to water, like e.g. in a bathroom. Consequently, the daily chewing agent according to the invention can be used when driving a car, during work, while watching television etc., thereby providing much more freedom to the user.

Daily chewing of chewing gum according to the invention in replacement of the conventional toothbrush with toothpaste is of particular advantage to certain groups of people. Army and navy personnel stationed abroad and possibly in areas with poor facilities, such as sparse access to clean water, need not carry a conventional toothbrush and toothpaste. The same applies to scientists and explorers working for extended periods of time in remote areas.

Chewing on a daily basis means chewing at least once a day in average seen over a period of e.g. a month. For improved cleaning effect of the chewing gum according to the invention it is preferred that chewing on a daily basis for tooth cleaning involves daily chewing of several pieces of the chewing gum. This will prolong the effects of teeth cleaning. The chewing on a daily basis for tooth cleaning can involve at least chewing in the morning and chewing in the evening. The chewing on a daily basis for tooth cleaning preferably involves chewing after a meal in order to neutralize food remains in the mouth, and chewing after every main meal consumed during the day is of particular advantage for maintaining clean teeth. Pieces of the chewing gum can be chewed several times per day, such as four or five times or more per day, and needless to say one fresh piece or more fresh pieces of chewing gum should be used for every new period of chewing.

Preferably, the individual piece of chewing gum is for chewing for a predetermined period during which various agents are released into the mouth. The predetermined period can e.g. be from about 1 to about 5 minutes, or for longer than 5 minutes. It is preferred that the individual piece of chewing gum is for chewing for a period in the range from about 5 minutes to about 20 minutes, preferably longer than 10 minutes, which period allows active agents in the chewing gum to be released and given a sufficient time to affect the teeth and gingiva, and thereby e.g. break down plaque, calculus, provide fresh breath etc. This period provides sufficient time for release of the active agents. The individual piece of chewing gum can also be for chewing for longer than 20 minutes.

According to an embodiment the chewing gum comprises gum base, at least one ingredient selected from the group consisting of whitening agents and fresh-breath agents, and at least two ingredients having at least two of the following effects: anti-plaque effect, anti-gingivitis effect, anti-calculus effect, or re-mineralization effect. It has appeared that a chewing gum based on gum base including at least one active cosmetic ingredient and at least two therapeutic ingredients can make the chewing gum very suitable as a chewing agent to replace daily tooth brushing.

In a further development of this embodiment at least 55% of said at least two ingredients is released after 5 minutes chewing when measured according to Ph. Eur. Version 5.0, January 2005, paragraph 2.9.25 (volume 1 page 260).

In a further or alternative development of this embodiment at least 30% of said at least one ingredient is released after 5 minutes chewing when measured according to Ph. Eur. Version 5.0, January 2005, paragraph 2.9.25 (volume 1 page 260).

As the skilled person would realise, the desired therapeutic effects are provided by several of the following agents: anti-plaque agents, anti-gingivitis agents, anti-calculus agents and re-mineralization agents. In most cases, although deviations sometimes may be desirable, one of the two or more active therapeutic ingredients should be an anti-plaque agent to prevent plaque formation on teeth and also remove plaque from teeth. In one embodiment the two or optionally three active therapeutic ingredients belongs to the same category i.e. anti-plaque agents, anti-gingivitis agents, anti-calculus agents, or re-mineralization agents. In an alternative embodiment the active therapeutic ingredients present in the chewing gum belong to different categories.

The at least one active cosmetic ingredient serves to improve the feeling of cleanness and freshness in the mouth subsequent to use of the chewing gum according to the invention.

Preferably, the active ingredients can be released from the chewing gum during chewing in an amount sufficient for constituting the daily dental care. The active ingredients are provided in the chewing gum in amounts sufficient for daily dental care, which means that they can be released from the chewing gum in amounts sufficient to provide the desired effect on the teeth and oral cavity.

Useful active ingredients are now described more closely.

Whitening Agents

By the term "whitening agents" as used herein is meant any agent, which is able to modify the colour of the teeth or to remove or bleach intrinsic or extrinsic stains on or in tooth surfaces for example by oxidising organic pigments or chromogens in the tooth.

The whitening agents are conveniently selected from teeth colour modifying substances that may be considered among the oral care actives useful in the chewing gum according to the invention. These substances are suitable for modifying the colour of the teeth in order to satisfy the consumer. Examples of such whitening agents are those listed in the CTFA Cosmetic Ingredient Handbook, 3.sup.rd Edition, Cosmetic and Fragrances Association Inc., Washington D.C. (1982), which are incorporated herein by reference. Specific examples include talc, mica, magnesium carbonate, calcium carbonate, calcium pyrophosphate, baking soda, Icelandic moss, bamboo, sodium hexa-metaphosphate, magnesium silicate, aluminium magnesium carbonate, silica, titanium dioxide, zinc oxide, red iron oxide, brown iron oxide, yellow iron oxide, black iron oxide, ferric ammonium ferrocyanide, manganese violet, ultramarine, nylon powder, polyethylene powder, methacrylate powder, polystyrene powder, silk powder, crystalline cellulose, starch, titanated mica, iron oxide titanated mica, bismuth oxychloride, and mixtures thereof. Typical levels are from about 0.05% to about 20%, preferably from about 0.1% to about 15% and most preferably from about 0.25% to about 10%, by weight, of the composition.

Whitening agents for use herein may also comprise materials that remove or bleach intrinsic or extrinsic stains on or in tooth surfaces. Examples of such whitening agents are peroxides, metal chlorites, perborates, percarbonates, peroxyacids, persulphates, and combinations thereof. Suitable peroxide compounds include hydrogen peroxide, urea peroxide, calcium peroxide, carbamide peroxide and mixtures thereof. Suitable metal chlorites include calcium chlorite, barium chlorite, magnesium chlorite, lithium chlorite, sodium chlorite and potassium chlorite. As additional bleaching substances hypochlorite, and chlorine dioxide may be mentioned. A preferred percarbonate is sodium percarbonate. Preferred persulphates are oxones. The content of these substances is dependent on the available oxygen or chlorine. The content of these ingredients in the chewing gum according to the invention is generally in the range from about 0.1% to about 35%, preferably from about 1% to about 25% and most preferably from about 5% to about 10%, by weight of the chewing gum.

In a preferred embodiment the whitening agent is selected from the group consisting of baking soda, Icelandic moss, Icelandic moss extract, bamboo, bamboo extract, calcium pyrophosphate, calcium carbonate, sodium hexa-metaphosphate, nature identical substitutes thereof, and mixtures thereof.

In another embodiment whitening agents are selected from the group consisting of baking soda, Icelandic moss, bamboo, calcium pyrophosphate, calcium carbonate, and sodium hexa-metaphosphate.

In the most preferred embodiment the whitening agents are selected from $NaHCO_3$, calcium carbonate, calcium pyrophosphate, titanium dioxide, and sodium hexa-metaphosphate.

Fresh-Breath Agents

By the term "fresh-breath agents" as used herein is meant any agent, which is able to control mouth-odor-causing bacteria, as for example agents which are able to control hydrogen sulphide-forming bacteria, as well as any agent which is able to absorb, adsorb, bind or otherwise complex the volatile oral malodour materials.

The fresh-breath agents are preferably selected from agents for oral malodour control, which include a wide variety of materials. Suitable in the chewing gum according to the invention are anti-microbial agents. Such agents may include 5-chloro-2-(2,4-dichlorophenoxy)-phenol, commonly referred to as triclosan, and described in the Merck Index, 11$^{th}$ Edition, (1989), pp 1529 (entry No. 9573) in U.S. Pat. No. 3,506,720, and in European Patent publication No. 0 251 591, phthalic acid and its salts including, but not limited to those disclosed in U.S. Pat. No. 4,994,262, preferably magnesium mono-potassium phthalate, chlorohexidine (Merck Index, No. 2090), alexidine (Merck Index, No. 222), hexetidine (Merck Index, No. 4624), sanguinarine (Merck Index, No. 8320), benzalkonium chloride (Merck Index, No. 1066), salicylanilide (Merck Index, No. 8299), domiphen bromide (Merck Index, No. 3411), cetylpyridinium chloride (CPC) (Merck Index, No. 2024), tetradecylpyridinium chloride (TPC), N-tetradecyl-4-ethylpyridinium chloride (TDEPC), octenifine, delmopinol, octapinol, and other piperidine derivatives, nicin preparations, zinc/stannous ion agents, antibiotics, such as augmentin, amoxicilline, tetracycline, doxycycline, hexadine, minocycline, and metronidazole, and analogues and salts of the above, methyl salicyclate, and mixtures of any of the above.

Illustrative zinc sources in the form of compounds with fresh breath properties for use as fresh-breath agents are zinc oxide, zinc silicate, zinc carbonate, zinc acetate, zinc phosphate, zinc stannate, zinc tetrafluoroborate, zinc hexafluorosilicate, zinc citrate, zinc benzoate, zinc oxalate, zinc stearate, zinc chloride, zinc sulfate, zinc nitrate, zinc phenolsulfonate, zinc carboxymethylsuccinate, and the like. The zinc compounds may also be present as a complex, with a complexing agent such as polyethylenimine or ethylenediamine tetraacetic acid.

A further group of natural extracts which are useful for their oral malodour control benefits include extracts obtained from the tea (green tea, red tea, white tea and black tea), honey suckle, coriander, thyme, propolis, tea tree oil, barberry bark, Champex®, sunphenon, applephenon, gold thread, magnolia plants or mixtures thereof. It is preferred that chewing gum according to the present invention comprise from about 0.01% to about 5%.

Extracts suitable for use in the present invention can be obtained from any part of the plant including the leaf, stem, bark, pulp, seed, flesh, juice, root and mixtures thereof. In the context of the present invention the term "extract" is intended to encompass infusions, liquid extracts, liquid concentrates of extracts, fractionated extracts and powdered extracts of the plants/berries/fruits etc. Extracts may be obtained by any conventional technique, such as water extraction, ethanol extraction or methanol extraction where appropriate. It is within the standard procedure of a skilled person to perform an appropriate extraction procedure in order to obtain an extract comprising the beneficial substances extracted from the plants, berries or fruits for use in the present invention.

By the term "nature identical substitute" as used herein is meant any natural or artificial compound or combination of compounds, which has a chemical structure identical to that found in nature. Most often a nature identical substitute is found as the main functional component of an extract or as a mixture of two or more of the main functional components in an extract. By the term "functional component" as used herein is meant the component performing the function of whitening the teeth, when mentioned in connection with whitening agents, or performing the function of providing the fresh-breath, when mentioned in connection with fresh-breath agents, etc. No nature identical substitutes can be found for inorganic compounds. The nature identical substitute may be prepared by use of chemical synthesis, by chemical modification of a compound of natural origin or by use of any enzymatical reaction pathway. The term is well known within the art and, therefore, a skilled person will appreciate whether an agent mentioned may or may not be found as a nature identical substitute.

The following essential oils are also known to have antimicrobial activity and are therefore optionally used in the chewing gum according to the present invention. By the term "essential oil" as used herein is meant any oil that impart the characteristic odors of plants. Oils, which are suitable for use in the present invention, include thymol, geraniol, carvacrol, hinokitiol, eucalyptol, catechol (particularly 4-allyl catechol), and mixtures thereof.

Another class of oral malodour control agents include absorbents. These are used to absorb, adsorb, bind or otherwise complex the volatile oral malodour materials. Examples of such agents include talc, mushroom extract, zeolite, cyciodextrin, silica shell and mixtures thereof. Such materials are preferably used in a range from about 0.5% to about 10%, preferably from about 1% to about 5%, by weight of the chewing gum.

In a preferred embodiment the fresh-breath agent is selected from the group consisting of a zinc source, coriander, coriander extract, green tea, green tea extract, propolis, propolis extract, tea tree oil, barberry bark, barberry bark extract, hexetidine, champes, sunphenol, applephenol, red tea, red tea extract, white tea extract, thyme extract, and mixtures thereof.

In another embodiment fresh-breath agents are selected from the group consisting of zinc acetate, coriander, green tea, propolis, tea tree oil, barberry bark, hexetidine, champes, sunphenol, applephenol, red tea, green tea extract, white tea and thyme extract.

In the most preferred embodiment the fresh-breath agents are selected from the group consisting of green tea extract, zinc acetate, 2-isopropyl-5-methyl-phenol (thymol), and eucalyptus.

Anti-Plaque Agents

Plaque is defined as a bacteria-containing substance that adheres to the surfaces of the teeth as well as on other surfaces of the oral cavity. Hence, by the term "anti-plaque agents" as used herein is meant any agent, which is able to prevent or inhibit the formation and accumulation of bacterial deposits on the surfaces of the oral cavity or to degrade or remove existing bacterial deposits on the surfaces of the oral cavity.

Examples of anti-plaque agents include xylitol and other anti-microbial agents. The inhibition effects of the xylitol on oral microbes may have better effect when used in conjunction with an extract since the extract is also acting to disable the microbes. Anti-plaque agents include fluoride ion sources.

Typical examples of active ingredients that are particularly desirable from considerations of anti-plaque effectiveness, safety and formulation include: naficillin, oxacillin, vancomycin, clindamycin, erythromycin, trimethoprim-sulphamethoxazole, rifampin, ciprofloxacin, broad spectrum penicillin, amoxicillin, gentamicin, ceftriazoxone, cefotaxime, chloramphenicol, clavunate, sulbactam, probenecid, doxycycline, spectinomycin, cefixime, penicillin G, minocycline, beta-lactamase inhibitors; meziocillin, piperacillin, aztreonam, norfloxacin, trimethoprim, ceftazidime, dapsone; halogenated diphenyl ethers, e.g. 2',4,4'-trichloro-2-hydroxydiphenyl ether (Triclosan), 2,2'-dihydroxy-5,5'-dibromo-diphenyl ether; halogenated salicylanilides, e.g. 4',5-dibromosalicylanilide, 3,4',5-trichlorosalicylanilide, 3,4',5-tribromosalicylanilide, 2,3,3',5-tetrachloro-salicylanilide, 3,3,3',5-tetrachloro-salicylanilide, 3,5-dibromo-3'-trifluoromethyl-salicylanilide, 5-noctanoyl-3'-trifluoromethyl-salicylanilide, 3,5-dibromo-4'-trifluoromethyl-salicylanilide, 3,5-dibromo-3'-trifluoromethyl-salicylanilide (Fluorophene); benzoic esters, e.g. methyl-p-hydroxybenzoic ester, ethyl-p-hydroxybenzoic ester, propyl-p-hydroxybenzoic ester, butyl-p-hydroxybenzoic ester; halogenated carbanilides, e.g. 3,4,4'-trichlorocarbanilide, 3-trifluoromethyl-4, 4'-dichlorocarbanilide, or 3,3,4'-trichlorocarbanilide; phenolic compounds (including phenol and its homologs, mono- and poly-alkyl and aromatic halo-phenol and their homologs), e.g. phenol, 2-methyl-phenol, 3-methyl-phenol, 4-methyl-phenol, 4-ethyl-phenol, 2,4-dimethyl-phenol, 2,5-dimethyl-phenol, 3,4-dimethyl-phenol, 2,6-dimethyl-phenol, 4-n-propyl-phenol, 4-n-butyl-phenol, 4-n-amyl-phenol, 4-tert-amyl-phenol, 4-n-hexyl-phenol, 4-n-heptyl-phenol, 2-methoxy-4-(2-propenyl)-phenol (Eugenol), 2-isopropyl-5-methyl-phenol (Thymol), mono- and polyalkyl- and aralkyl-halophenols, methyl-p-chlorophenol, ethyl-p-chlorphenol, n-propyl-p-chlorophenol, n-butyl-p-chlorophenol, n-amyl-p-chlorophenol, sec-amyl-p-chlorophenol, n-hexyl-p-chlorophenol, cyclohexyl-p-chlorophenol, n-heptyl-p-chlorophenol, n-octyl-p-chlorophenol, o-chlorophenol, methyl-o-chlorophenol, ethyl-o-chlorophenol, n-propyl-o-chlorophenol, n-butyl-o-chlorophenol, n-amyl-o-chlorophenol, tert-amyl-o-chlorophenol, n-hexyl-o-chlorophenol, n-heptyl-o-chloropenol, p-chlorophenol, o-benzyl-p-chlorophenol, o-benzyl-m-methyl-p-chlorophenol, o-benzyl-m,m-dimethyl-p-chlorophenol, o-phenylethyl-p-chlorophenol, o-phenylethyl-m-methyl-p-chlorophenol, 3-methyl-p-chlorophenol, 3,5-dimethyl-p-chlorophenol, 6-ethyl-3-methyl-p-chlorophenol, 6-n-propyl-3-methyl-p-chlorophenol, 6-iso-propyl-3-methyl-p-chlorophenol, 2-ethyl-3,5-dimethyl-p-chlorophenol, 6-sec-butyl-3-methyl-p-chlorophenol, 2-iso-propyl-3,5-dimethyl-p-chlorophenol, 6-diethylmethyl-3-methyl-p-chlorophenol, 6-iso-propyl-2-ethyl-3-methyl-p-chlorophenol, 2-sec-amyl-3,5-dimethyl-p-chlorophenol, 2-diethylmethyl-3,5-dimethyl-p-chlorophenol, 6-sec-octyl-3-methyl-p-chlorophenol, p-bromophenol, methyl-p-bromophenol, ethyl-p-bromophenol, n-propyl-p-bromophenol, n-butyl-p-bromophenol, n-amyl-p-bromophenol, sec-amyl-p-bromophenol, n-hexyl-p-bromophenol, cyclohexyl-p-bromophenol, o-bromophenol, tert-amyl-o-bromophenol, n-hexyl-o-bromophenol, n-propyl-m,m-dimethyl-o-bromophenol, 2-phenyl-phenol, 4-chloro-2-methyl-phenol, 4-chloro-3-methyl-phenol, 4-chloro-3,5-dimethyl-phenol, 2,4-dichloro-3,5-dimethyl-phenol, 3,4,5,6-tetrabromo-2-methylphenol, 5-methyl-2-pentylphenol, 4-isopropyl-3-methylphenol, 5-chloro-2-hydroxydiphenyl-methane; resorcinol and its derivatives, e.g. resorcinol, methylresorcinol, ethyl-resorcinol, n-propyl-resorcinol, n-butyl-resorcinol, n-amyl-resorcinol, n-hexyl-resorcinol, n-heptyl-resorcinol, n-octylresorcinol, n-nonyl-resorcinol, phenyl-resorcinol, benzyl-resorcinol, phenylethyl-resorcinol, phenylpropyl-resorcinol, p-chlorobenzyl-resorcinol, 5-chloro-2,4-dihydroxydiphenyl-methane, 4'-chloro-2,4-dihydroxydiphenyl-methane, 5-bromo-2,4-dihydroxydiphenyl-methane, 4"-bromo-2,4-dihydroxydiphenyl-methane; and bisphenolic compounds, e.g. bisphenol A, 2,2'-methylene-bis-(4-chlorophenol), 2,2'-methylene-bis-(3,4,6-trichlorophenol) (hexachlorophene), 2,2'-methylene-bis-(4-chloro-6-bromophenol), bis-(2-hydroxy-3,5-dichlorophenyl)-sulfide, and bis-(2-hydroxy-5-chlorobenzyl)-sulfide.

Illustrative of polyphosphate compounds with plaque-inhibiting properties are dialkali metal and tetraalkali metal pyrophosphate and mixtures thereof in a hydrated or unhydrated form. Illustrative of pyrophosphate salts are $Na_2H_2P_2O_7$, $Na_4P_2O_7$ and $K_4P_2O_7$. Other suitable polyphosphates include hydrated or unhydrated alkali metal tripolyphosphates such as $Na_5P_3O_{10}$ and $K_5P_3O_{10}$.

Plaque buffers such as urea, calcium lactate, calcium glycerophosphate and strontium polyacrylates, ammonium carbonate and vitamins such as Vitamins A, C and E are also included.

Nutraceuticals and nutritional supplements may also be added to chewing gums as active agents against plaque. Among these are herbs and botanicals that include, but are not limited to chamomile, echinacea, Eucalyptus and green tea.

Metal cations can also be used as anti-bacterial and anti-plaque agents. The metal cations are selected from the metals of Group 5 (V, Nb, Ta); Group 6 (Cr, Mo, W); Group 7 (Mn, Tc, Re); Group 8 (Fe, Ru, Os); Group 9 (Co, Rh, Ir); Group 10 (Ni, Pd, Pt); Group 11 (Cu, Ag, Au); Group 12 (Zn, Cd, Hg); Group 14 (Ge, Sn, Pb); Group 16 (Se, Te, PO); and mixtures thereof. Preferably the metal cation is selected from any monovalent or divalent cation selected from the group consisting of zinc, manganese, copper, iron, cobalt, silver, selenium, tin and vanadium; preferably from the group consisting of zinc, manganese, copper, iron, silver, and tin; more preferably from the group consisting of zinc, copper, silver and tin and most preferably from the group consisting of zinc and tin.

Illustrative of zinc compounds with plaque-inhibiting properties are zinc oxide, zinc silicate, zinc acetate, zinc carbonate, zinc phosphate, zinc stannate, zinc tetrafluoroborate, zinc hexafluorosilicate, zinc citrate, zinc benzoate, zinc oxalate, zinc stearate, zinc chloride, zinc sulfate, zinc nitrate, zinc phenolsulfonate, zinc carboxymethylsuccinate, and the like. The zinc compound also can be in the form of a complex, with a complexing reagent such as polyethylenimine or ethylenediamine tetraacetic acid.

A wide variety of metal cation salts are useful in the present invention. These include so called "water-insoluble salts" which have a solubility of less than about 0.5 g per 100 ml at 25° C. and "water soluble salts" which have a solubility of greater than or equal to about 0.5 g per 100 ml at 25° C. It is also possible to use mixtures of these salts. Such mixtures can have several advantages in the compositions of the present invention since they are likely to have different complexing properties with the polyphosphate anions. In addition they have different release rates in the saliva and can therefore act to provide controlled release profiles. Examples of salts that are suitable for use herein include acetate, ammonium sulphate, bromide, chloride, chromate, citrate, di-thionate, fluorosilicate, tartrate, fluoride, formate, iodide, nitrate, phenol sulphate, salicyclate, sulphate, gluconate, succinate, glycerophosphate, lactate and mixtures thereof.

In a preferred embodiment the anti-plaque agent is selected from the group consisting of a zinc source, ammonium carbamate, eucalyptus, eucalyptus extract, cranberry, cranberry extract, xylitol, chlorhexidine, seaweed, seaweed extract, epigallocatechin gallate, osteopontin, baking soda, nature identical substitutes thereof, and mixtures thereof.

In another embodiment the anti-plaque agents are selected from the group consisting of zinc acetate, ammonium carbamate, eucalyptus, cranberry, xylitol, chlorhexidine, seaweed, osteopontin and baking soda.

In the most preferred embodiment the anti-plaque agents are selected from the group consisting of aronia, eucalyptus, immuglobuline-lysozyme (e.g. Ig-lyt or IG-LY 4023), xylitol, green tea extract, and zinc acetate.

Anti-Gingivitis Agents

Gingivitis is defined as an inflammation of the gums surrounding the teeth caused by a build up of plaque or food particles. Hence by the term "anti-gingivitis agents" as used herein is meant any agent, which is able to prevent or inhibit an inflammation of the gums surrounding the teeth caused by a build up of plaque or food particles. Consequently, anti-gingivitis agents can be anti-inflammatory agents, such as salicylic acid derivatives (e.g. aspirin), paraminophenol derivative (e.g. acetaminophen), indole and indene acetic acids (indomethacin, sulindac and etodalac), heteroaryl acetic acids (tolmetin, diclofenac and ketorolac), aryl propionic acid derivatives (ibuprofen, naproxen, ketoprofen, fenopren, oxaprozine), anthranilic acids (mefenamic acid, meclofenamic acid), enolic acids (piroxicam, tenoxicam, phenylbutazone and oxyphenthatrazone), lactic acid bacteria (LAB), Osteopontin (ONP), IG-Lyt, hexefine, Aloe Vera, chlorhexedine, myrrh, or sage.

Examples of anti-gingivitis agents also include psychotherapeutic agents, such as thorazine, serentil, mellaril, millazine, tindal, permitil, prolixin, trilafon, stelazine, suprazine, taractan, navan, clozaril, haldol, halperon, loxitane, moban, orap, risperdal, alprazolam, chlordiaepoxide, clonezepam, clorezepate, diazepam, halazepam, lorazepam, oxazepam, prazepam, buspirone, elvavil, anafranil, adapin, sinequan, tofranil, surmontil, asendin, norpramin, pertofrane, ludiomil, pamelor, vivactil, prozac, luvox, paxil, zoloft, effexor, welibutrin, serzone, desyrel, nardil, parnate, or eldepryl.

In a preferred embodiment the anti-gingivitis agent is selected from the group consisting of chlorhexidine, myrrh, myrrh extract, neem, neem extract, sage, sage extract, aloe vera, aloe vera extract, hexatidine, osteopontin, quince, quince extract, immuglobuline-lysozyme powder, nature identical substitutes thereof, and mixtures thereof. As an example of an immuglobuline-lysozyme powder, the powder sold under the tradename IG-LY 4023 (obtainable from Pedersen's Laboratorium, Vejle, Denmark) may be mentioned.

In another embodiment the anti-gingivitis agents are agents selected from the group consisting of chlorhexidine, myrrh, neem, sage, aloe vera, hexatidine, osteopontin, quince, and immuglobuline-lysozyme powder (Tradename IG-LY 4023, obtainable from Pedersen's Laboratorium, Vejle, Denmark).

In the most preferred embodiment the anti-gingivitis agents are agents selected from the group consisting of osteopontin and immuglobuline-lysozyme (Ig-lyt).

Re-Mineralization Agents

Re-mineralization is defined as the reversal of demineralisation of tooth enamel. Hence, by the term "re-mineralization agents" as used herein is meant any agent, which is able to build up the enamel as well as any agent, which is able to inhibit the demineralization of tooth enamel.

Examples of such re-mineralization agents include pH adjusting agents, which may also be added to make the composition safe for oral tissues. These pH adjusting agents, or buffers, can be any material that is suitable to adjust the pH of the composition. Suitable materials include sodium bicarbonate, sodium phosphate, sodium hydroxide, ammonium hydroxide, potassium hydroxide, sodium stannate, triethanolamine, citric acid, hydrochloric acid, sodium citrate, calcium, fluoride, Phoscal, dicalcium phosphate, Osteopontin (ONP), monosodium phosphate, trisodium phosphate, sodium hydroxide, sodium carbonate, pectin, benzocaine, analgesics, sanguinarine extract, metronidazole, strontium chloride, potassium nitrate, carrageenan, cough and cold remedies, and the like.

In a preferred embodiment the re-mineralization agent is selected from the group consisting of calcium fluoride, osteopontin, a chemical complex between casein phosphoprotein and nanoclusters of amorphous calcium phosphate, nature identical substitutes thereof, and mixtures thereof. In a particular embodiment of the invention the compound sold under the tradename phoscal, which is a chemical complex between casein phosphoprotein and nanoclusters of amorphous calcium phosphate, is selected as the re-mineralization agent.

In another embodiment the re-mineralization agents are selected from the group consisting of calcium, fluoride, osteopontin, and a chemical complex between casein phosphoprotein and nanoclusters of amorphous calcium phosphate (tradename phoscal).

In the most preferred embodiment the re-mineralization agents are selected from the group consisting of sodium fluoride, dicalcium phosphate, and carbamide.

As chewing gum stimulates saliva, and a wide range of active ingredients can be added to the chewing gum according to the invention that promotes re-mineralization or alternatively inhibits de-mineralization, the re-mineralization effect of the chewing gum exceeds the effect of brushing of teeth.

Anti-Calculus Agents

Calculus may be defined as hardened deposit composed of mineralised plaque and saliva. Hence, by the term "anti-calculus agents" as used herein is meant any agent, which is able to prevent or reduce the formation of hardened deposit composed of mineralised plaque and saliva.

Anti-calculus agents suitable for use in the chewing gum according to the invention include phosphates, pyrophosphates, alkali-metal pyrophosphates, polyphosphates, phosphonates, polyphosphonates and mixtures of any of these. Pyrophosphates are among the best known for use in dental care products. The pyrophosphate salts useful in the present invention include the di-alkali metal pyrophosphate salts, tetra-alkali metal pyrophosphate salts and mixtures of any of these in their unhydrated as well as hydrated forms are the preferred species. Di-sodium di-hydrogen pyrophosphate ($Na_2H_2P_2O_7$), tetra-sodium pyrophosphate ($N_4P_2O_7$), and tetrapotassium pyrophosphate ($K_4P_2O_7$) and mixtures thereof are specific examples.

Additional suitable anti-calculus agents include polyacrylates and other polycarboxylates, such as those disclosed in U.S. Pat. No. 3,429,963, U.S. Pat. No. 4,304,766, and U.S. Pat. No. 4,661,341, polyepoxysuccinates, such as those disclosed in U.S. Pat. No. 4,846,650, ethylenediaminetetraacetic acid as disclosed in British Patent No. 490,384, nitrilotriacetic acid and related compounds as disclosed in U.S. Pat. No. 3,678,154, polyphosphonates as disclosed in U.S. Pat. No. 3,737,533, U.S. Pat. No. 3,988,443, and U.S. Pat. No. 4,877,603.

In a preferred embodiment the anti-calculus agent is selected from the group consisting of vitamin C, citric acid, acetic acid, nature identical substitutes thereof, and mixtures thereof.

In another embodiment anti-calculus agents are selected from the group consisting of vitamin C, citric acid, and acetic acid.

In a preferred embodiment the chewing gum comprises at least one whitening agent, at least one fresh-breath agent, and at least three ingredients providing at least three of the following effects: anti-plaque effect, anti-gingivitis effect, anti-calculus effect, and/or re-mineralization effect. In this embodiment the ingredients providing at least three of said effects optimise the overall effect of the chewing gum on the teeth and oral cavity in general.

In a further embodiment the chewing gum comprises at least one whitening agent, at least one fresh-breath agent, and at least four ingredients having the following effects: anti-plaque effect, anti-gingivitis effect, anti-calculus effect, and re-mineralization effect. This embodiment has excellent qualities in respect of cleaning teeth and improving the conditions in the oral cavity.

The chewing gum according to the invention is preferably a chewing gum wherein at least 55% of the active therapeutic ingredients are released after 5 minutes of chewing when measured according to Ph. Eur. (European Pharmacopoeia) Version 5.0, January 2005, paragraph 2.9.25 (volume 1 page 260). Preferably at least 75% of the active therapeutic ingredients are released after 15 minutes of chewing when measured according to Ph. Eur. Version 5.0, January 2005, paragraph 2.9.25 (volume 1 page 260). In this manner it is secured that sufficient amounts of the active therapeutic ingredients are released within the preferred chewing time of 5 to 20 minutes.

Moreover, the chewing gum according to the invention is preferably a chewing gum wherein at least 30% of the active cosmetic ingredients are released after 5 minutes of chewing when measured according to Ph. Eur. Version 5.0, January 2005, paragraph 2.9.25 (volume 1 page 260). Preferably at least 50% of the active cosmetic ingredients are released after 10 minutes of chewing when measured according to Ph. Eur. Version 5.0, January 2005, paragraph 2.9.25 (volume 1 page 260). This preferred embodiment of the invention provides for sufficient amounts of the active cosmetic ingredients to be released within the preferred chewing time of 5 to 20 minutes.

In a preferred embodiment the chewing gum according to the invention further comprises one or more taste ingredients selected from sweeteners, high-potent sweeteners and flavours. When taste ingredients like sweeteners and flavours are used, these are normally admixed to the gum base or to the active ingredients. The addition of taste ingredients acts to make the user chew on the gum for longer time, because it is pleasant to do so. The taste ingredients do in this manner increase the effects of the therapeutic agents and the cosmetic agents.

In an embodiment the chewing gum is manufactured from traditional coherent gum. In this manner the active agents and optionally other ingredients are mixed into the gum base mass. The mixing operation may take place at elevated temperature to decrease the viscosity of the chewing gum formulation thereby facilitating the mixing. After the mixing the chewing gum formulation is normally sent through rollers to form sheets of chewing gum from which pieces of chewing gum are punched or scored out.

In general, traditional coherent chewing gum is manufactured by sequentially adding the various chewing gum ingredients to a commercially available mixer known in the art. After the ingredients have been thoroughly mixed, the gum mass is discharged from the mixer and shaped into the desired form such as by rolling into sheets and cutting into sticks, extruding into chunks or casting into pellets. Alternatively, coherent chewing gum may be manufactured by extrusion.

Generally, the ingredients are mixed by initially melt the gum base and feed it to the running mixer. The base may also be melted in the mixer itself. Colour or emulsifiers may also be added at this time. A softening agent such as glycerine may also be added at this time, along with syrup and a portion of the bulking agent. Further portions of the bulking agent may then be added to the mixer. A flavouring agent is typically added with the final portion of the bulking agent.

It will be recognised to those skilled in the art, that variations of the above-described procedure may be used.

In another, preferred embodiment the chewing gum is manufactured as compressed chewing gum tablets. In one embodiment the chewing gum tablet is a compressed mixture of gum base and ingredients of active agents, and optionally of other ingredients. Thus, the gum base is present as granules or powder and is mixed with the active agents, which may also be present as granules or powder, and optionally other ingredients like taste ingredients can also be added to the mixture. Taste ingredients are in a preferred embodiment selected from the group consisting of sweeteners, high-potent sweeteners and flavours. The mixture is filled into a press that presses the mixture to form compressed chewing gum tablets. Use of granules is in particular an advantage when one or more of the active ingredients are sensitive towards elevated temperatures as the mixing and pressing can be done at low temperature, e.g. normal room temperature.

In another embodiment directed at the manufacture of chewing gum tablets of a compressed mixture or blend of materials, gum base granules are included in said mixture before the mixture is pressed into tablets. In a further embodiment ingredients of active agents are present in said gum base granules. These ingredients can be added to the gum base material during the preparation thereof.

Not all active agents need to be added to the gum base material. Preferably, temperature sensitive agents are added to the mixture of gum base granules or gum base powder just before the materials are blended or mixed for conveyance to a tablet pressing apparatus.

In a preferred embodiment at least one fraction of said active agents is present only in some of said gum base granules, and at least another fraction of said active agents is present only in others of said gum base granules. By making several types of gum base granules containing their respective active agents it is possible to effectively keeping the respective active agents apart, because the final blending or mixing of materials before pressing the tablets does not cause the materials to be actually intermixed into a homogenous mass, but instead the blend or mixture remains a blend or mix of powder, granules etc.

In a further embodiment the ingredients of active agents present in said mixture in one or both of the following forms: granules and powder. And in another embodiment gum base powder is included in said mixture. In addition or as an alternative chewing gum powder can be included in said mixture. This can be of advantage, e.g. if the gum base and other ingredients have been mixed together into a chewing gum mass which is then brought into powder form, such as by freezing and milling. Furthermore, chewing gum granules can be included in said mixture, and also in this embodiment it is possible to include ingredients of active agents in said chewing gum granules; and in a further development at least one fraction of said active agents is present only in some of said chewing gum granules, and at least another fraction of said active agents is pre-sent only in others of said chewing gum granules.

In an embodiment a fraction of said ingredients of active agents is included in said gum base. This can be an advantage, e.g. to control the release rate of the active agents, or to obtain a desirable separation of different active agents in a compressed chewing gum tablet until chewing of the gum. Some agents, like zinc sources and osteopontin, can interact in undesired manners, and this can be avoided by intermixing the one agent into the gum base material, which is formed to gum base granules or chewing gum powder, and by adding powder or granules of the other agent together with additional agents and possible taste ingredients to the blend prepared just before the tablets are pressed. The blend can be a blend of powders, a blend of granules or a blend of powders and granules. The blend is compressed into tablets.

In one embodiment the fraction of said ingredients of active agents can be present in the gum base during mixing thereof prior to shaping the gum base material into gum base granules. During this mixing the temperature is elevated, so the most temperature sensitive agents are preferably added to the blend prepared after the gum base has been shaped into granules or powder.

The fraction of agents intermixed into the gum base can amounts to at least 20% by weight of the total contents of active agents in the chewing gum tablet, and even higher values, such as amounts of at least 30% or at least 40% are also possible.

In other embodiments the chewing gum according to the invention can be centre filled gum (centre filled with liquid, gel or powder), coated gum or gum formed as sticks. Preferably the gum has an average weight of about 0.5 to 5 g, preferably from 1.5 to 3.5 g.

In one embodiment of the chewing gum according to the invention the chewing gum is layered. The chewing gum can comprise two or three or more layers. The layers can be placed on top of each other or side by side. Optionally the layers have different colours.

When the chewing gum is layered it is possible to provide embodiments wherein different active therapeutic ingredients are present in different layers in the chewing gum. This is particular advantageously when the active therapeutic agents are mutual reactive. When the agents are present in different layers undesired reactions between the agents might be avoided.

Similar conditions apply in corresponding embodiments where different active cosmetic ingredients are present in different layers in the chewing gum.

In one embodiment at least one of the layers is substantially free of gum base. In another embodiment one or more agents are present in the chewing gum in only one of the layers. And in a further embodiment one or more agents located in the chewing gum in two of the layers are not present in all layers. And in a further embodiment two or more agents are present in the chewing gum in different layers.

For some embodiments of the chewing gum it is preferred that the chewing gum is coated. A coating may protect the active agents from decomposition e.g. caused by oxygen. Moreover, a coating may contribute to maintain a desired moisture content in the chewing gum or other physical conditions required to avoid break down of an active ingredient. The coating may be a hard coating or a film coating. In an embodiment of the invention the chewing gum is consequently coated with an outer coating. Preferably the outer coating is a hard coating.

When the chewing gum has a coating at least one active therapeutic agent and/or at least one active cosmetic agent may be present in the coating. Such an embodiment can for instance be advantageously when a rapid release of one or more active agents is desirable.

In a preferred embodiment of the invention the hard coating is a coating selected from the group consisting of a sugar coating and a sugarless coating and a combination thereof.

In a further embodiment of the invention the hard coating comprises 50 to 100% by weight of a polyol typically selected from the group consisting of sorbitol, maltitol, mannitol, xylitol, erythritol, lactitol and isomalt.

In an alternative embodiment of the invention the outer coating is an edible film comprising at least one component selected from the group consisting of an edible film-forming agent and a wax. In a preferred embodiment of the invention the film-forming agent is selected from the group consisting of a cellulose derivative, a modified starch, a dextrin, gelatine, shellac, gum arabic, zein, a vegetable gum, a synthetic polymer and any combination thereof.

In an embodiment of the invention the outer coating comprises at least one additive component selected from the group consisting of a binding agent, a moisture absorbing component, a film forming agent, a dispersing agent, an anti-sticking component, a bulking agent, a flavouring agent, a colouring agent, a pharmaceutically or cosmetically active component, a lipid component, a wax component, a sugar, an acid and an agent capable of accelerating the after-chewing degradation of the degradable polymer.

In an embodiment the outer coating is a soft coating comprising a sugar free coating agent.

The invention also encompasses an embodiment, in which the chewing gum comprises at least one barrier layer. A barrier layer may serve to separate two active agents that will react when mixed. Optionally the barrier layer is a layer in a layered tablet e.g. a chewing gum tablet comprising three or more layers.

According to an embodiment of the invention the one or more anti-plaque agents can constitute from 0.01 to 50% by weight of the chewing gum, and high values of up to 70% by weight of anti-plaque agents is relevant only with respect to xylitol, which may be added in a very high amount to act as an anti-plaque agent etc. Preferably the anti-plaque agents constitute 0.03-50%, and values of 0.05 to 35% of the chewing gum are also possible.

Preferably, the one or more anti-gingivitis agents can constitute from 0.01 to 20% by weight, more preferred 0.03-12% by weight of the chewing gum.

Preferably, the one or more anti-calculus agents can constitute from 0.01 to 20% by weight, more preferred 0.03-15% by weight of the chewing gum.

Preferably, the one or more re-mineralization agents can constitute from 0.01 to 20% by weight, more preferred 0.02-10% by weight of the chewing gum.

Preferably, the one or more whitening agents can constitute from 0.01 to 20% by weight, more preferred 0.03-12% by weight of the chewing gum.

Preferably, the one or more fresh-breath agents can constitute from 0.01 to 20% by weight, more preferred 0.02-8% by weight of the chewing gum.

The above listed ranges for content of active ingredients have proven to provide an effective amount of active therapeutic and cosmetic ingredients. The total amount of active ingredients should, however, preferably not exceed approximately 35%, such as 35.5%, by weight based on the total weight of the chewing gum (however, in case of xylitol the amount of active ingredients can exceed 70% as explained above). Preferably the active therapeutic ingredients constitute about 5 to 20%, and the active cosmetic ingredients constitute about 2 to 12% of the chewing gum based on the total weight of the chewing gum.

In an embodiment of the chewing gum according to the invention the gum base further includes at least one antibacterial agent, preferably selected from xylitol, chlorhexidine, neem, green tea, thyme, and Icelandic moss, and the antibacterial agent preferably constitutes about 0.4 to 7.5% of the chewing gum.

The present invention also relates to chewing gum possessing tooth cleaning effects for round the year daily use as the major tooth cleaning agent. Thus, the above described chewing gum has qualities that makes is highly suitable for use as the major tooth cleaning agent in providing personal oral health to a person round the year, and significantly reducing the risk of abrasive damage on the teeth.

Typically, the chewing gum comprises a water-soluble bulk portion, a water-insoluble chewable gum base portion and typically water-insoluble flavouring agents. The water-soluble portion dissipates with a portion of the flavouring agent over a period of time during chewing. The gum base portion is retained in the mouth throughout the chew.

The insoluble gum base typically comprises elastomers, resins, fats and oils, waxes, softeners and inorganic fillers. Elastomers may include polyisobutylene, isobutylene-isoprene copolymer and styrene butadiene rubber, as well as natural latexes such as chicle. Resins may include polyvinylacetate and terpene resins. Fats and oils may also be included in the gum base, including tallow, hydrogenated and partially hydrogenated vegetable oils, and cocoa butter. Commonly employed waxes include paraffin, microcrystalline and natural waxes such as beeswax and carnauba.

In one embodiment, the insoluble gum base constitutes between about 5 to about 95 percent by weight of the gum. More preferably the insoluble gum base comprises between 10 and 50 percent by weight of the gum, such as from 35 to 46%, or from about 20 to about 35 percent by weight of the gum.

Particularly interesting elastomeric or resinous polymer compounds which advantageously can be used in a process according to the invention include polymers which, in contrast to currently used elastomers and resins, can be degraded physically, chemically or enzymatically in the environment after use of the chewing gum, thereby giving rise to less environmental pollution than chewing gums based on non-degradable polymers, as the used degradable chewing gum remnants will eventually disintegrate and/or can be removed more readily by physical or chemical means from the site where it has been dumped.

Preferably if degradable, the chewing gum comprises at least two different biodegradable polymers wherein at least one of said biodegradable polymers comprises a polyester polymer.

At least one of said at least two different biodegradable polymers may comprise a polyester produced through reaction of at least one alcohol or derivative thereof and at least one acid or derivative thereof. Another or other of said at least two different biodegradable polymers may comprise a polyester obtained by polymerization of at least one cyclic ester.

The gum base typically also includes a filler component. The filler component may be selected from magnesium and calcium carbonate, sodium sulphate, ground limestone, silicate compounds such as magnesium and aluminum silicate, kaolin and clay, aluminum oxide, silicium oxide, talc, titanium oxide, mono-, di- and tri-calcium phosphates, cellulose polymers, such as wood, and combinations thereof.

When present, the filler may constitute between about 5 and about 60 percent by weight of the gum base. Preferably, the filler comprises about 5 to about 50 percent by weight of the gum base.

Gum bases typically also contain softeners, including glycerol monostearate and glycerol triacetate. Furthermore, gum bases may also contain optional ingredients such as antioxidants, colours, and emulsifiers, such as lecithin, sweeteners and flavours. The present invention contemplates employing any commercially acceptable gum base.

The water-soluble portion of the chewing gum may further comprise softeners, sweeteners, flavouring agents and combinations thereof. Softeners are added to the chewing gum in order to optimize the chew ability and mouth feel of the gum. Softeners, also known in the art as plasticizers or plasticizing agents, generally constitute between about 0.1 to about 15 percent by weight of the chewing gum. Softeners contemplated by the present invention include glycerine, lecithin, and combinations thereof. Further, aqueous sweetener solutions such as those containing sorbitol, hydrogenated starch hydrolysates, corn syrup and combinations thereof may be used as softeners and binding agents in gum.

In a preferred embodiment of the chewing gum according to the invention the chewing gum further comprises one or more taste ingredients selected from sweeteners, high-potent sweeteners and flavours, or mixtures thereof. The sweeteners may e.g. be sweeteners like sucrose, dextrose, dextrins, maltose, trehalose, D-tagatose, dried invert sugar, ribose, fructose, levulose, galactose, glucose, maltodextrin, polydextrose, isomalt, sorbitol, sorbitol syrup, mannitol, xylitol, hexaresorcinol, maltitol, isomaltol, erythriol, lactitol, xylose, tagatose and hydrogenated starch hydrolysates (maltitol syrup). The high potent sweeteners can include the dipeptides aspartame, neotame and alitame; N-sulfonylamides such as saccharin including the salts thereof and acesulfam including the salts thereof; sulfamates such as cyclamate including the salts thereof; chlorinated sugar derivatives such as sucralose; Terpenoid glycosides such as Rebaudioside-A, Stevioside and Glyhyrrhizin; proteins such as thaumatin and monellin and Di-hydrochalcones.

A variety of one or more flavouring agents may be used. Flavouring agents suitable for use in the present invention include natural, natural-identical, and/or artificial flavouring substance, or mixtures thereof, in their solid and/or in their liquid state. The person skilled in the art will recognize that natural and artificial flavouring agents may be combined in any sensorially acceptable blends. Some examples of suitable tastes are peppermint, lemon, and orange.

When taste ingredients like sweeteners and flavours are used, these are normally admixed to the gum base or the active ingredients. Taste ingredients in the chewing gum stimulate the user to chew for a prolonged period of time, which again have the advantages that the active ingredients have a longer period to be released and affect teeth and gingival surfaces.

The chewing gum according to the invention can in one embodiment be substantially free of abrasives. However, the chewing gum preferably contains some amount of abrasive and polishing agents, in particular of a type softer than dental enamel and dentine. As such abrasives and polishing agents are included in the chewing gum they will act only on the outer portions of the teeth where they cannot cause an abrasive effect on the teeth because the enamel is strong. And the chewing gum cannot press down gingiva and any abrasive or polishing agents present in the chewing gum cannot act on the vulnerable innermost portions of the teeth.

Consequently, a polishing material can be any material that does not abrade dental enamel and dentine. Typical materials include silica gels and precipitates, aluminas, phosphates, and mixtures thereof. Specific examples include dicalcium orthophosphate dihydrate, calcium pyrophosphate, Bamboo, tricalcium phosphate, hydrated alumina, beta calcium pyrophosphate, calcium carbonate, sodium polymetaphosphate, sodium hexametaphosphate, Calgen, Giltex, Quadrafos, Hagan phosphate, micromet, calcium phosphate dibasic, calcium monohydrogen phosphate, dicalcium orthophosphate secondary calcium phosphate, carbonic acid calcium salt, cacti, calcichew, calcidia, citrical, aragonite, calcite, valerite, aluminum oxide, alumina, silicon dioxide, silica, silicic anhydride, and resinous abrasive materials such as particulate condensation products of urea and formaldehyde and others such as disclosed in U.S. Pat. No. 3,070,510. Mixtures of polishing agents can also be used.

The silica polishing materials generally have an average particle size ranging between about 0.1 to about 30 microns; and preferably from about 5 to about 15 microns. The polishing agent can be precipitated silica or silica gels, such as the silica xerogels described in U.S. Pat. No. 3,538,230 or in U.S. Pat. No. 3,862,307. Preferred are the silica xeropgels marketed under the name "Syloid" by the W. R. Grace and Company, Davison Chemical Division. Also preferred are the precipitated silica materials such as those marketed by the 3. M. Huber Corporation under the trade name "Zeodent", particularly the silica carrying the designation "Zeodent 119". The types of silica dental polishing agents useful in the chewing gum of the present invention are described in more details in U.S. Pat. No. 4,340,583. When present in the chewing gum, the polishing agents in the chewing gum is generally present in the range from about 6% to about 70%, such as from about 10% to about 50%, by weight of the chewing gum.

The present invention relates, as is apparent from the above explanation, to a teeth cleaning method, wherein daily teeth cleaning is performed by chewing a chewing gum instead of using a toothbrush.

It is preferred that the chewing gum, when chewed on a daily basis as a tooth cleaning agent, provides a) a whitening effect corresponding to at least 50% of the whitening effect of daily brushing of teeth with a new toothbrush, b) a fresh-breath effect corresponding to at least 100% of the fresh-breath effect of daily brushing of teeth with a new toothbrush, c) an anti-plaque effect corresponding to at least 60% of the anti-plaque effect of daily brushing of teeth with a new toothbrush, d) an anti-gingivitis effect corresponding to at least 65% of the anti-gingivitis effect of daily brushing of teeth with a new toothbrush, e) a re-mineralization effect corresponding to at least 65% of the re-mineralization effect of daily brushing of teeth with a new toothbrush.

It is also preferred that the daily use provides an anti-calculus effect corresponding to at least 25% of the anti-calculus effect of daily brushing of teeth with a new toothbrush. And naturally a substantially lower abrasive effect than the abrasive effect caused by daily brushing of teeth with a new toothbrush is also provided.

A new toothbrush has good properties in respect of tooth cleaning, but a toothbrush will unavoidably cause abrasive damage at least to some degree. However, during use the toothbrush will gradually lose its tooth cleaning properties, but still be able to cause abrasive damage. Consequently, in a relative short time the toothbrush cleaning properties in respect of whitening, plaque and gingivitis will decrease to a level of about 50-65% compared to the properties for a new toothbrush. The chewing gum according to the invention is in its nature always new, because a new piece of chewing gum is used each time the teeth are cleaned by chewing the gum. The tooth cleaning obtained by chewing the gum may perform significantly better than a used toothbrush. As most people do not change toothbrush every day, but commonly use the same toothbrush for a month or more, the cleaning properties of such a brush are not optimal.

In a preferred embodiment of the chewing gum according to the invention the whitening effect corresponds to at least 65%, preferably at least 85%, and more preferably at least 100%, of the whitening effect of daily brushing of teeth with a new toothbrush.

In a preferred embodiment of the chewing gum according to the invention the anti-plaque effect corresponds to at least 65%, preferably at least 85%, and more preferably at least 100%, of the anti-plague effect of daily brushing of teeth with a new toothbrush.

In a preferred embodiment of the chewing gum according to the invention the anti-gingivitis effect corresponds to at least 75%, preferably at least 85%, and more preferably at least 100%, of the anti-gingivitis effect of daily brushing of teeth with a new toothbrush.

In a preferred embodiment of the chewing gum according to the invention the re-mineralization effect corresponds to at least 75%, preferably at least 85%, and more preferably at least 100%, of the re-mineralization effect of daily brushing of teeth with a new toothbrush.

In a preferred embodiment of the chewing gum according to the invention the anti-calculus effect corresponds to at least 50%, preferably at least 65%, and more preferably at least 100%, of the anti-calculus effect of daily brushing of teeth with a new toothbrush.

It is estimated that that the overall effect of chewing gum for dental cleaning compared to brushing teeth can be set to at least 70% relative to brushing teeth. This estimate is based on correct use of a new toothbrush (2 minutes brushing by a skilled user) compared to chewing of chewing gum for 5 to 20 minutes. Depending on the number of active ingredients in the chewing gum according to the present invention the overall effect of chewing gum for cleaning of teeth may exceed 100%.

BRIEF DESCRIPTION OF THE SINGLE VIEW OF THE DRAWING

Examples of the invention will now be explained below with reference to examples and to the very schematic drawing, which in FIG. 1 illustrates an estimate of the efficacy of the chewing gums tested (C.G)(chewing for 5 to 20 minutes) for dental care purposes compared with tooth brushing (T.B)(new toothbrush and correct tooth brushing for 2 minutes)

DETAILED DESCRIPTION OF THE INVENTION

Gum base refers in general to any commercially available gum base suitable for production of chewing gum. Such gum bases are well-known and available on the market and normally comprise natural and/or synthetic resins and optionally other ingredients. The gum base may be biodegradable.

Chewing gum is the final product, including gum base, active agents and optional other ingredients such as taste ingredients and coloring agents. The chewing gum is ready to use by the consumer for cleaning teeth.

Active therapeutic ingredient means any agent that has an active therapeutic effect on the teeth and the oral environment including gingiva. Some active therapeutic ingredients may be active against more than one condition, e.g. function as both anti-plaque agent and anti-calculus agent and they are in the present context listed under both functions.

Anti-plaque agents include any agent that has a specific therapeutic effect of preventing or inhibiting plaque or of minimizing or removing existing plaque formations.

Anti-gingivitis agents include any agent that has a specific therapeutic effect of preventing or inhibiting gingivitis or of minimizing or removing existing gingivitis.

Anti-calculus agents include any agent that has a specific therapeutic effect of preventing or inhibiting calculus or of minimizing or removing existing calculus formations.

Re-mineralization agents include any agent that has a specific therapeutic effect in improving the degree of re-mineralization of the teeth or avoiding de-mineralization of the teeth.

Active cosmetic ingredients are ingredients that have cosmetic effect on the teeth or the oral cavity, i.e. to improve the appearance of the teeth including odour.

Whitening agents include any agent capable of bleaching or whiten teeth.

Fresh-breath agents include any agent that provides a fresh and pleasant-smelling breath.

All percentages (%) are weight percentages unless otherwise stated.

The chewing gum according to the invention can be conventional chewing gum pieces, compressed chewing gum tablets, sticks, centre-filled chewing gum with the centre filled with liquid, gel or powder. Moreover, the active ingredients, flavour and sweetener may be encapsulated to avoid undesired reactions during storage.

The line at 1 indicates the efficacy of a toothbrush and the columns indicates the efficacy of chewing gum in respect of plaque, whitening, fresh breath, gingivitis, calculus, re-mineralization and abrasive damage, respectively. As indicated by the line, the overall efficacy of tested chewing gum compared to tooth brushing is about 67%. The individual effects can be improved by adding more active ingredients and/or by combining ingredients so that the efficacy is raised above 70%, such as an efficacy that exceeds 100% or better efficacy than tooth brushing.

In respect of plaque (efficacy approx. 60% for the tested chewing gum) the removal of plaque and/or inhibition of plaque formation can been improved, e.g. by adding zinc acetate to the chewing gum, which will enhance the effect to be close to or better than the efficacy for brushing teeth. In addition, the chewing gum according to the invention will be better than brushing teeth in real life due to the fact that the effect from chewing gum reaches places the toothbrush cannot reach. An in vivo plaque study performed by the inventors shows that e.g. zinc acetate worked in the "hard-to-reach" places with high efficiency.

Moreover, a clinical test has demonstrated that chewing gum with calcium pyrophosphate clinically whitens teeth. Presently, the effect almost matches the effect of a toothbrush with toothpaste. However, by using other agents the whitening effect will reach 100% as compared with tooth brushing.

The fresh breath effect is already better than if brushing teeth, as the chewing gum according to the invention has a much longer contact time with the volatile sulphur compounds to be eliminated. Correct tooth brushing last 2 minutes whereas chewing of chewing gum last for at least 5 minutes.

With respect of the anti-gingivitis effect, chewing gum according to the invention already match this effect compared to brushing of teeth, as the contact time is longer as with brushing teeth, thereby allowing the active substances longer time to affect the infected gingiva.

As chewing gum stimulates saliva, and a wide range of active ingredients can be added to the chewing gum according to the invention that promotes re-mineralization or alternatively inhibits de-mineralization, the re-mineralization effect of the chewing gum exceeds the effect of brushing of teeth.

The chewing gum according to the present invention substantially has no damaging effect on softer portions of the teeth or on the gingival tissue, and this parameter is naturally dramatically better than brushing teeth.

EXAMPLE 1

The chewing gum in the following example was manufactured from commercially available gum base (Danfree, available from Gumlink A/S, Vejle, Denmark) mixed with sweeteners, taste ingredients and active ingredients. The chewing gum was manufactured as a two-layer product and the gum material for the two layers was produced with the following ratios:

Formulation 1:

| | |
|---|---|
| Gum base | 60.00% |
| Sorbitol | 18.20% |
| Peppermint powder | 1.50% |
| Menthol powder | 0.30% |
| Dicalciumphosphate | 2.70% |
| Green tea | 5.00% |
| Baking soda | 0.40% |
| Calcium carbonate | 4.10% |
| Calcium pyrophosphate | 6.50% |
| Sucralose | 0.25% |
| Magnesium stearate | 0.50% |
| *Eucalyptus* powder | 0.50% |

Formulation 2:

| | |
|---|---|
| Gum base | 30.00% |
| Xylitol | 68.80% |
| Peppermint powder | 0.50% |
| Menthole powder | 0.20% |
| Magnesium stearate | 0.50% |

The gum base was granulated (GALA underwater pelletizer) to form granules with diameters in the range of approximately 0.5-1.5 mm and mixed with the active ingredients.

The particulate mixture of formulation 1 (1.5 g) was filled into a tablet pressing machine and compressed to form a first layer. Then 0.7 g pure gum base granules were filled into the tablet machine and compressed onto the first layer to form a barrier layer. Finally 2 g of formulation 2 particulate material was filed into the tablet pressing machine and compressed.

The resulting cylindrical shaped layered chewing gum tablets had an average weight of about 4.2 g and a diameter of about 8 mm.

The chewing gum was evaluated for inhibition of plaque formation in a clinical study.

The test subjects abstained from all oral hygiene for 2 days and either chewed the gum five times per day or used no gum (Plaque scores were assigned using the Modified Quickly-Hein (MQH) index). The result demonstrated that chewing gum comprising xylitol was significantly more effective in inhibiting the formation of plaque on teeth when used as the only means of oral hygiene for two days. Additionally, it was most efficient in areas that are often missed during tooth brushing.

In conclusion, the results demonstrate that the chewing gum containing xylitol is able to reduce dental plaque formation. Moreover, the chewing gum has an ability to make dental plaque less adhesive and thus easier to remove during chewing. As a further benefit, xylitol inhibit bacterial growth and thereby inhibit tooth decay.

The chewing gum was also evaluated for its whitening effect. The chewing gum comprising calcium pyrophosphate not only results in whiter teeth by stain removal, it also helps to prevent further stain after consumption of foods and beverages.

Clinical studies on the inhibition of stain over a 14 days period showed that when chewing, chewing gum according to the invention 20 minutes each day, compared to chewing, chewing gum with 4.5% calcium carbonate, commercially available on the market, the inhibition of stain was considerably improved.

The dicalcium phosphate in the chewing gum improves the re-mineralization rate of the teeth.

Green tea provided excellent fresh breath properties in the chewing gum.

Further studies of the effects of the chewing gum according the invention were performed as described below. For the purpose of the studies two types of chewing gum were prepared as compressed chewing gum tablets. The formulations of the chewing gum tablets used in Examples 2 to 4 are shown in Table A below.

TABLE A

| Ingredient | A: According to invention | B: Placebo | C: According to the invention |
|---|---|---|---|
| CRP base | 20.00 | 20.00 | 20.00 |
| Base | 20.00 | 20.00 | 20.00 |
| Sorbitol | 30.39 | 52.10 | 31.01 |
| Maltitolsyrup | 5.00 | 5.00 | 5.00 |
| Lecithine | 0.2. | 0.20 | 0.20 |
| Green tea extract | 1.25 | | 1.25 |
| Phenol | 0.52 | | 0.52 |
| Aronia | 1.25 | | 1.25 |
| Osteopontin | 0.02 | | |
| Zinc | 0.06 | | 0.06 |
| Fluoride | 0.03 | | 0.03 |
| $NaHCO_3$ | 1.04 | | 1.04 |
| Caiciumcarbonate | 3.00 | | 3.00 |
| Dicaliciumphosphate | 2.30 | | 2.30 |
| Calciumpyrophosphate | 6.80 | | 6.80 |
| titandioxid | 1.00 | | 1.00 |
| Thyme | 0.24 | | 0.24 |
| Acesulfame | 0.20 | 0.20 | 0.20 |
| Aspartame | 0.20 | 0.20 | 0.20 |
| Peppermint | 1.00 | 1.00 | 1.00 |
| *Eucalyptus* | 1.00 | 1.00 | 1.00 |
| Menthol | 0.30 | 0.30 | 0.30 |
| Xylitol | 4.20 | | 4.20 |
| Total | 100.00 | 100.00 | 100.00 |

Four different studies were performed:
A study for assessing oral malodor
A study for assessing re-mineralisation
A study for assessing whitening
A study for inhibiting dental plaque The four studies were performed and supervised by a qualified dentist in order to assess the effect of the chewing gum according to the invention.

EXAMPLE 2

Study for Assessing Oral Malodor

The purpose of this study was to demonstrate the efficacy of chewing gum containing green tea extract and zinc in reducing oral malodor (OM) as compared to a placebo.
Methods & Materials:

The investigation was a longitudinal study, which determined efficacy of the chewing gum in reducing oral malodor. A total of 20 subjects with self proclaimed oral malodor (OM) that has been verified by an organoleptic judge (OJ) were selected for this randomized clinical trial. Subjects were instructed to chew the provided gum five times a day for 20 minutes each time for a period of seven days.

Qualified subjects completed a demographic and a medical history survey and were assessed for degrees of OM. The qualifying score of the subjects as determined by self-proclamation and OJs was minimum of 2 or above on the 5-point malodor scale. Baseline (day 0) and post treatment (day 7) examinations included: 1) organoleptic tests 2) oral soft tissue evaluation 3) OralChroma. The results of baseline and post treatment examinations for organoleptic scores were scored on the 5-point malodor scale as described below. 20 subjects were randomly assigned to the one of the following groups with 10 subjects to each group: Group 1: Subjects using chewing gum containing the active ingredient, Group 2: Subjects using placebo chewing gum. All groups were instructed in routine oral hygiene procedures. Subjects in Groups 1 and 2 were instructed on the use of the chewing gum. Test articles were then distributed to subjects of each group. The groups were requested to perform the assigned procedures at home for a period of seven days. Subjects were asked to keep a daily diary during the seven-day period to record compliance to the instructions and procedures given. At the end of the seven-day period, the clinical post treatment examinations previously mentioned were repeated on each subject. The data collected at the baseline examination and at the post treatment examination were then compared and statistically analyzed.

20 adult male/female subjects were enrolled to complete the evaluation as required. Subjects were eligible to enter the study if they met the following selection criteria: over the age of 18 years and in good general health, willingness to sign the informed consent form and comply with protocol procedures, a minimum OM score of 2 on the 5-point malodor scale, a minimum of 16 natural teeth including at least 4 molars, and availability to complete the seven-day study. They were excluded if they had gross oral pathoses, orthodontic devices, partial or complete dentures, any systemic disease, periodontal disease, or gross oral hygiene neglect, were pregnant or lactating women, were chronic smokers, or were on prophylactic antibiotic coverage for routine dental therapy and used systemic antibiotics for a period of more that seven days prior to the study, or were participating in other dental or investigational trials.

An IRB approved informed consent statement was reviewed and signed by each subject. After final eligibility was ascertained by the inclusion/exclusion criteria, a distinct subject number was assigned to each subject.
Diagnostic Tests:
Organoleptic Assessment:

Two OJs trained and calibrated according to the protocol developed by UHRG & University of Minnesota made two separate assessments on each subject. Each subject was instructed to close their mouths without swallowing for a period of two minutes. After two minutes the subject breathed out gently, at a distance of 10 cm from the nose of the OJ. The odors were assessed according to the 5-point scale: 1=No perceived odor, 2=Faint odor, 3=Moderate odor, 4=Strong odor, 5=Extremely strong odor.
Clinical Examinations:
Oral Soft Tissue Assessment:

The oral cavity was assessed for irregular tissue, canker sores, or cancer lesions. Subjects with gross periodontal disease, calculus, bridges, or dentures were excluded from the study.
OralChroma:

OralChroma is a gas chromatographer and typically consistent measurements may vary due to differences in human breath gases. Subjects were instructed to avoid eating, drinking, brushing, flossing or scraping their tongue for at least 2 hours prior to providing breath samples. The subject held the syringe in his/her sealed oral cavity for 30 seconds without touching the tip of the syringe with his/her tongue. After the 30-second period the syringe was filled with a breath sample. The syringe was wiped after removal from the subject's mouth to remove any saliva and the needle was placed onto the syringe for injection into the machine.

The time between the removal of the syringe from the subject's mouth and injecting the sample into the Oral-Chroma was minimized to avoid any changes in the concentration of the breath gases as the temperature of the sample decreases from the body temperature to room temperature. Only ½ ml of the breath sample was injected into the Oral-Chrome. A new syringe was used for each subject to avoid contamination.

All subjects completed a daily account of their assigned procedures in order to record compliance with the requirements of the protocol as well as any complaints or comments.

Test Products:

The chewing gum test products were supplied for each subject by the sponsor in coded containers as defined in the study protocol. The test products were assigned after each subject was enrolled and assigned a subject number.

Results:

Subjects in Group 1 who used the chewing gum containing the active ingredient positively reported that they enjoyed the great taste and freshness of the mouth that the gum provided, and released a good blast of taste in the beginning. They also reported that the tasty gum was long lasting and worked for reducing OM. Subjects in Group 1 negatively reported that the gum tasted medicinal and had a bad aftertaste after the first initial minutes of chewing. Subjects also reported that the taste went away quickly, and after chewing for 20 minutes it felt like chewing cardboard and left the mouth and tongue dry. Other subjects reported that there was excessive saliva produced from chewing, or that the gum started to break apart into loose sand-like particles.

Subjects in Group 2 who used the placebo positively reported that the gum had a great taste with a good flavor and made the mouth and tongue feel clean, leaving fresh breath even after chewing. Subjects also reported that they felt the gum worked to reduce OM and helped to get rid of food particles in the mouth. Subjects in Group 2 negatively reported that they did not like the flavor of the gum; some reported that the flavor was not strong enough and faded too fast, others reported that the flavor was too strong. Subjects also reported that chewing the gum in the morning did not appear to help reduce OM due to the bad taste on the tongue, it was too difficult to chew two pieces of gum at the same time, and that the gum became stiff while chewing.

Statistical Analysis was performed to compare various OM parameters. Absolute mean changes and percentage mean changes for all the OM parameters over time and between each group was performed and p-values were calculated. 20 subjects were enrolled in the study, nine subjects in Group 1 completed the study, and eight subjects in Group 2 completed the study.

Eight variables were measured in each subject, once on day 0 and once on day 7. The means and standard error for each group and the mean difference, the standard error of the mean difference and the corresponding p-values for comparison for the groups were calculated. The p values that are statistically significant are ($p<0.10$).

The analysis of covariance in a repeated measures model was used. The chewing gum A containing the active product was found to be significantly more effective overall in reducing morning breath.

The results are shown in Table X and Table Y below.

TABLE X

Summary of Baseline and Day 7 Oral Malodor Assessment Scores for Subjects Who Completed the 1 Week Study

| Parameter | Treatment | Summary | Baseline Difference Mean ± SD | Significance | Summary | Day 7 Difference mean +/− SD | Significance |
|---|---|---|---|---|---|---|---|
| Organo-leptic 1 | Active | 3.82 ± 0.32 | Placebo 0.32 ± 0.47 | P = 0.5032 | 1.00 ± 0.28 | Placebo −1.88 ± 0.42 | P < 0.0001 |
| | Placebo | 3.50 ± 0.34 | | | | | |
| Organo-leptic 2 | Active | 3.91 ± 0.32 | Placebo 0.51 ± 0.46 | P = 0.2742 | 1.10 ± 0.29 | Placebo −1.78 ± 0.43 | P = 0.0002 |
| | Placebo | 3.40 ± 0.32 | | | | | |
| Oral Chroma $H_2S$ (ng/10 ml) | Active | 3.03 ± 0.41 | Placebo 0.02 ± 0.60 | P = 0.9772 | 0.77 ± 0.28 | Placebo −2.33 ± 0.43 | P < 0.0001 |
| | Placebo | 3.01 ± 0.44 | | | | | |
| Oral Chroma $CH_3SH$ (ng/10 ml) | Active | 2.38 ± 0.58 | Placebo −1.46 ± 0.84 | P = 0.0907 | 0.57 ± 0.46 | Placebo −3.65 ± 0.69 | P < 0.001 |
| | Placebo | 3.85 ± 0.61 | | | | | |
| Oral Chroma $(CH_3)_2S$ (ng/10 ml) | Active | 1.40 ± 0.23 | Placebo 0.38 ± 0.34 | P = 0.2709 | 0.42 ± 0.18 | Placebo −0.60 ± 0.26 | P = 0.0305 |
| | Placebo | 1.02 ± 0.24 | | | | | |
| Oral Chroma $H_2S$ (ppb) | Active | 300.73 ± 32.34 | Placebo 145.53 ± 46.86 | P = 0.0037 | 74.20 ± 26.23 | Placebo −96.68 ± 39.35 | P = 0.0194 |
| | Placebo | 155.20 ± 33.91 | | | | | |
| Oral Chroma $CH_3SH$ (ppb) | Active | 133.18 ± 23.75 | Placebo 54.78 ± 34.41 | P = 0.1018 | 45.80 ± 17.69 | Placebo −29.08 ± 26.54 | P = 0.2811 |
| | Placebo | 75.40 ± 24.90 | | | | | |
| Oral Chroma | Active | 10.27 ± 5.56 | Placebo | P = 0.6378 | 2.90 ± 4.57 | Placebo | P = 0.1821 |

TABLE X-continued

Summary of Baseline and Day 7 Oral Malodor Assessment Scores for Subjects Who Completed the 1 Week Study

| Parameter | Treatment | Summary | Baseline Difference Mean ± SD | Significance | Summary | Day 7 Difference mean +/− SD | Significance |
|---|---|---|---|---|---|---|---|
| $(CH_3)_2SH$ (ppb) | | | −3.83 ± 8.06 | | | −9.35 ± 6.86 | |
| | Placebo | 14.10 ± 5.83 | | | | | |

Table X. Summary of eight OM parameters at baseline (day 0) and day 7. Organoleptic 1 and Organoleptic 2 represent the mean OM assessment scores of OJ1 and OJ2, respectively. The chewing gum containing the active ingredient was statistically significant (p < 0.001) in reducing oral malodour compared to the placebo group for both the scores from Organoleptic 1 and Organoleptic 2. The OralChroma measures hydrogen sulphide ($H_2S$), methyl mercaptan ($CH_3SH$), and dimethyl sulphide (($CH_3)_2SH$) in ng/10 ml and parts per billion (ppb). The chewing gum containing the active ingredient was statistically significant (p < 0.001) for reducing hydrogen sulphide compared to the placebo. Methyl mercaptan was also statistically significantly (p < 0.001) reduced compared to the placebo.

TABLE Y

Summary of the Difference in Oral Malodor Scores After 7 days of treatment

| Parameter | Treatment | Summary | Difference mean +/− SD | Significance |
|---|---|---|---|---|
| Organoleptic 1 | Active | −2.80 ± 0.22 | Placebo −2.05 ± 0.33 | P < 0001 |
| | Placebo | −0.75 ± 0.25 | | |
| | Control | 0.00 ± 0.22 | | |
| Organoleptic 2 | Active | −2.08 ± 0.22 | Placebo −2.18 ± 0.33 | P < 0.0001 |
| | Placebo | −0.63 ± 0.25 | | |
| | Control | −0.10 ± 0.22 | | |
| Oral Chroma $H_2S$ (ng/10 ml) | Active | −2.35 ± 0.36 | Placebo −2.18 ± 0.54 | P = 0.0003 |
| | Placebo | −2.9A6 ± 0.38 | | |
| | Control | −0.20 ± 0.36 | | |
| Oral Chroma $CH_3SH$ (ng/10 ml) | Active | −1.,84 ± 0.39 | Placebo −1.93 ± 0.59 | P = 0.0038 |
| | Placebo | −0.01 ± 0.44 | | |
| | Control | −0.18 ± 0.39 | | |
| Oral Chroma $(CH_3)_2S$ (ng/10 ml) | Active | −1.03 ± 0.12 | Placebo −0.95 ± 0.18 | P = <0.0001 |
| | Placebo | −0.18 ± 0.12 | | |
| | Control | −0.18 ± 0.12 | | |
| Oral Chroma $H_2S$ (ppb) | Active | −222 ± 21.91 | Placebo −208.75 ± 32.86 | P = <0.0001 |
| | Placebo | −13.25 ± 24.49 | | |
| | Control | −38.9 ± 21.91 | | |
| Oral Chroma $CH_3SH$ (ppb) | Active | −77.60 ± 13.56 | Placebo −62.48 ± 20.34 | P = 0.0042 |
| | Placebo | −15.13 ± 15.16 | | |
| | Control | −6.90 ± 13.56 | | |
| Oral Chroma $(CH_3)_2SH$ (ppb) | Active | −7.50 ± 3.29 | Placebo −6.25 ± 4.93 | P = 0.2137 |
| | Placebo | −1.25 ± 3.67 | | |
| | Control | −0.30 ± 3.29 | | |

Table Y. Summary of differences in OM scores between baseline (day 0) and day 7. The chewing gum containing the active ingredient was statistically significant (p < 0.001) in reducing OM compared to the placebo for Organolaeptiv 1 and Organoleptic 2. The chewing gum containing the active ingredient was statistically significant (P < 0.001) in reducing dimethyl sulphide and hydrogen sulphide in ppb compared to the placebo.

EXAMPLE 3

Study for Assessing Re-Mineralization

Materials and Methods:
Demineralization Solution Preparation:

The demineralizing buffer solutions was made up of analytical-grade chemicals and deionized water. It contained 2.2 mM $CaCl_2$, 2.2 mM $NaH_2PO_4$, 0.05 M acetic acid and pH was adjusted with 1 M KOH to 4.4.

Artificial Enamel Carious Lesion Formation:

Sound extracted molars were cleaned of any soft tissue debris and inspected for cracks, hypoplasia, and white spot lesions under the stepreomicroscope. The teeth were then coated with acid-resistant varnish (Lancester, Germany), leaving a narrow 'window', approximately 1 mm wide, on the sound, intact surface of the buccal and/or lingual enamel. Each tooth was immersed, for 96 hours, in 10 ml of demineralizing solution in order to produce lesions of about 130-180 μm deep. The teeth were sectioned longitudinally through the lesions, approximately 100-150 μm thick, by a hard tissue microtome (Leica 1600, Wetzlar, Germany). Seventy two sections were randomly selected and equally divided into three groups, i.e. twenty-four sections per group. Every section was studied using PLM (Orthoplan, Leitz, Germany) and MRG (Softex ISR-20, JIRA, Japan), respectively, in order to record the depth and mineral content of the lesion at baseline before the 21-day intra-oral experimental period. The same evaluation techniques were utilized to record the lesion characteristics after the intra-oral period.

Prior to being attached to an intra-oral appliance, each section was painted, under a stereomicroscope, with acid-resistant varnish leaving only the lesion surface exposed to the oral environment. After the intra-oral test phase of the experiment, this nail varnish was removed by immersing each enamel section in acetone for 10 s and thoroughly rinsed with deionized water. The sections were stored in a 100% humidity environment until used. This was achieved by suspending the specimens, using dental floss, over deionized water in a beaker which was sealed with paraffin (Para film, USA).

Test Groups:

There were three experimental groups coded as A, B and C, respectively. Eighteen healthy volunteers in the age range of 20-33 years participated in this study. After being given verbal and written explanations of the experimental protocol, informed consent was obtained from all of the volunteers. The oral hygiene status of each individual was checked to confirm that they had good oral hygiene, no active dental caries, no enamel fluorosis, and no gingival/periodontal or mucosal pathology.

Experimental Protocol:

After the protocol has been approved by the Faculty Ethics Committee, upper and lower alginate impressions of the subject's dentition were taken, and plaster casts were constructed. A modified version of the lower appliance used in our previous study (Itthagarun et al., 2005) was custom made for each subject. Two enamel specimens were mounted horizontally parallel to each other in slightly recessed areas of the appliance, positioned just below the lingual aspect of the mandibular second premolars, giving four specimens per subject. The enamel sections were covered by gauze (Dacron®, C. R. Bard, Billerica, Mass.) to encourage the formation and accumulation of plaque on the surface of enamel. A total of 72 specimens were planned for the experiment i.e. 24 sections per group. The enamel specimens were evaluated for the lesion depth and mineral profile at baseline before being placed in the appliances. Each volunteer was then provided with the appliance without specimens before the actual intra-oral test phase of the experiment to resolve any irritation to the soft tissue that was caused by the appliance.

All of the participants were randomly divided in to 3 groups (six participants in each group):

Group A. Each subject was instructed to wear the appliance and chew a fluoride chewing gum [Gumlink®] for 20 minutes immediately after breakfast, lunch, dinner and after snacks (mid-morning and mid-afternoon) for a period of 21 days. They were also instructed to clean their teeth using a soft toothbrush once daily (morning) without toothpaste.

Group B. Each subject was instructed to wear the appliance and brush his/her teeth using a soft tooth brush twice daily (morning and night) for up to one minute with a pea sized amount of fluoridated toothpaste (FluoCalcin, 1000 ppmF).

Group C. Each subject was instructed to wear the appliance and brush his/her teeth with a soft tooth brush once daily (morning) for up to one minute without using toothpaste.

The diet of the volunteers was not altered instead it was standardized for all the subjects by recording their food intake for the first week and then giving back a copy of the record with a request that they maintain a similar diet throughout the experimental period. The subjects were also supplied with snack food in accordance with the plaque pH study by Jensen (1986) and instructed to consume two of the provided snacks each day; one mid-morning and one mid-afternoon so as to simulate between-meal snacks.

Subjects wore the intra-oral appliance all the time, for a period of 21 days, including eating and during sleep; it was only removed for tooth brushing. After 21 days, all of the appliances were returned to the operator, except for one from a volunteer in Group A, the enamel specimens were removed from the appliances and re-evaluated for their lesion depth, mineral profile and compared with the baseline data recorded before the intra-oral period.

1. Two subjects withdrew during the experiment, one from Group A and one from Group B. II. One subject from Group A had not returned the appliance by the time the results were analysed. III. Some of the specimens were broken during the experimental procedures. IV. The total numbers of the specimens at the time of data analysis were therefore 15, 18 and 18 for Groups A, B and C, respectively.

Evaluation Techniques

Qualitative Evaluation:

After imbibition of the sections in water, PLM was employed to evaluate qualitatively the body of the lesion in each of the enamel sections. The sections were expected to show a clear demarcation between sound enamel and an initial lesion. Any changes in the lesion during the experimental period could be detected from the photomicrographs which were taken at a standard magnification before and after experiment.

Quantitative Evaluation:

Enamel sections were exposed to X-ray irradiation at 10 kV and 3 mA for a period of one minute for each section. Standard Kodak chemicals were used for film development. After being developed, each film was mounted and captured in the IBAS 2000 system (Kontron, Germany), which enables automatic measurement of the lesion area and lesion depth both 'before' and 'after' treatment. Thus, an actual change or a percent change was calculated. An image analysis system (Macintosh Quadra 700, USA) was utilized to measure the amount of mineral change before and after treatment within the same lesion these values were used to make comparisons between the three test groups.

Results

The results are shown in Table Z below.

TABLE Z

Mean values (±SD) of lesion depth, maximum mineral content in the surface zone and the differences in the mineral content of the samples in the three treatment groups.

| Group (n) | Lesion depth (LD) Mean ± SD | Vmax Mean ± SD | Delta Z Mean ± SD |
|---|---|---|---|
| A Before | 174.6 ± 13.0 | 29.6 ± 6.3 | 8605 ± 629.6 |
| Chewing gum After †* | 158.4 ± 17.8 †* | 33.5 ± 6.8 †* | 7783 ± 902.2 |
| (15) % Change | 9.1 ± 9.6 *** | −14.4 ± 18.9 | 9.3 ± 9.7 *** |
| B Before | 161.5 ± 11.7 | 34.3 ± 4.3 | 7919 ± 591.5 |
| Fluoride Paste After †* | 155.9 ± 11.4 †* | 36.9 ± 4.5 †* | 7635 ± 570.2 |
| (18) % Change | 3.4 ± 1.2 *** | −7.5 ± 5.1 | 3.5 ± 1.3 *** |
| C Before | 169.6 ± 19.4 | 36.8 ± 11.3 | 8319 ± 987.8 |
| No-Toothpaste After †* | 175.7 ± 14.1 †* | 32.1 ± 9.8 †* | 8648 ± 715.8 |
| (18) % Change | −4.1 ± 5.9 *** | 11.7 ± 13.6 | −4.5 ± 6.1 *** |

† paired –t-test
* indicates a significant difference at $p < 0.05$
*** indicates a significant difference at $p < 0.0001$ [ANOVA and Student-Newman-Keuls tests]

PLM observation:

Photomicrographs taken under the PLM (Zeiss, Wetzlar, Germany) which was connected to a computer system (LeicaQuin, Leica, Germany), revealed that the mean and standard deviation (SD) of pre-treatment lesion depth, from each group, ranged from 161±11 μm to 175±14.1 μm. Among these pre-treatment lesion depths, no statistically significant result was obtained (p=0.0523, ANOVA).

The results from the lesion depth measurements after the trial period showed that the lesions were reduced by 9% (174.6±13.1→158.4±17.8), and 3% (161.5±11.7→155.9±11.4) in Groups A and B respectively, while an increase in the lesion depth of about 4% (169.6±19.4→175.7±14.1) was noted in Group C. These values were found to be statistically significant different (p<0.05, pair t-test). ANOVA and Student-Newman-Keuls (SNK) tests also confirmed a statistically significant difference among all treatment groups (p<0.0001).

MRG Observation:

After the 21 day intra-oral test period, the maximum mineral content in the surface zone ($V_m$) of the lesions in Groups A and B increased by 14% and 8% respectively, while the $V_m$ of the group C decreased by 11.7%. A paired -t- test confirmed a statistical significance between the before and after mineral contents in the surface zone of the lesions within each group (p<0.05). However, when comparisons were made among the treatment groups, ANOVA and SNK tests showed no statistically significant difference between Groups A and B (p>0.05), while Groups A and B were statistically significant different from Group C (p<0.0001).

After the 21 intra-oral period, ΔZ Values showed a decrease of 9% and 4% for Groups A and B, respectively (p<0.05, paired -t- test) while in Group C, the ΔZ values increased by 4%. A statistically significant difference was noted when comparisons were made among the three treatment groups (p<0.0001, ANOVA, SNK).

Summary:

The lesion characteristics recorded (Lesion depth, $V_{max}$, ΔZ) after the intra-oral period, of the lesions in all of the three groups, showed a significant difference from those before the treatment.

After chewing the fluoride containing chewing gums for 21 days, it was found that the mean lesion depth had reduced by 9%, the mineral content in the surface zone of the lesion had increased by 14% while the ΔZ had decreased by 9%.

After using the fluoride toothpaste, twice a day for 21 days, the mean lesion depth was found to have reduced by 3%, the mineral content in the surface zone of the lesion had increased by 7% while the ΔZ had decreased by 4%.

After the test period the specimens in the control group showed that their mean lesion depth increased by 4%, the mineral content at the surface zone of the lesion had decreased by 11% while the ΔZ had increased by 5%.

Although no significant difference was found when the $V_{max}$ data from the Group A (chewing gum) and Group B (fluoride toothpaste) were compared, there was a trend in the results indicating that Group A lesions showed better "healing efficacy" than Group B. However, these values might have reached a level of statistical significant difference if the sample size had been bigger.

Based on the lesion depth and ΔZ values, it appears that chewing a fluoride containing chewing gum 5 times a day could slow down the progress of demineralization more effectively than brushing twice a daily with a fluoride toothpaste.

EXAMPLE 4

Study for Assessing Whitening

A special laboratory method has been developed to determine the potential of chewing gums to remove dental stains. The general experimental design consists of using a specially-designed mechanical mastication device to treat stained teeth with chewing gum. (Developed by M. S. D., Ph.D. Carl J. Kleber)

The purpose of this study is to evaluate the whitening effect of chewing gum with different active ingredients (formulation A, Table 1) as well as a placebo gum without active ingredients (formulation B, Table 1) and compare the results to the whitening effect of brushing teeth with a toothbrush.

The difference in whiteness is measured quantitatively using a colorimeter.

To compare the effect of chewing gum and toothbrush 2 times brushing of 1 minute and 5 times chewing chewing gum of 20 minutes was chosen, in order to simulate a realistic daily use.

Materials & Methods

The chewing gum granules used contains the following raw materials (Table 1), where Baking Soda, Calcium Pyrophosphate, Calcium Carbonate and possibly Aronia and Titan, will be effective in the whitening process:

The chewing buffer is a ammoniumdihydrogenphosphat_ solution (1.38 g/L) were pH is adjusted to 7.4 with NaOH.

Specimens was prepared by Carl Kleber:

Squares of bovine dental enamel were embedded in clear polyester casting resin to provide 1.5 cm square blocks with the labial surface exposed. The specimens were rinsed with deionized water and attached to a staining apparatus in preparation for stain formation.

The tooth staining apparatus was designed to provide alternate immersion into the staining broth and air-drying of the specimens.

The staining broth was prepared by adding 1.02 g of instant coffee, 1.02 g of instant tea, 10 ml of red wine, and 0.75 g of gastric mucin to 250 ml of sterilized trypticase soy broth. Approximately 50 ml of a 24-hour *Micrococcus /uteus* culture was also added to the stain broth. The apparatus, with the enamel specimens attached and the staining broth in the trough was then placed in an incubator at 37° C. with the specimens rotating continuously through the staining broth and air. The staining broth was replaced once every 24 hours. With each broth change, the trough and specimens were rinsed and tooth brushed with deionized water to remove any loose deposits.

Stain Measurement:

The amount of the stain on the teeth was measured by taking colour readings with a Minolta spectrophotometer CM-2600d. Measurements over the entire visible colour spectrum were obtained using the CIELAB colour scale. This scale quantifies colour according to 3 parameters, L* (white-black value), a* (red-green chroma), and b* (yellow-blue chroma). In order to obtain reproducible readings, the stained enamel specimens were allowed to air-dry at room temperature for 30 minutes before colour measurements were made. At the end of a test period the stain was removed with sandpaper grain 600, in order to measure how much stain was available to remove.

Measurements were obtained by aligning the center of the 4-mm square segment of stained enamel directly over the 3-mm-diameter targeting aperture of the Minolta@ spectrophotometer. An average of 3 colour readings using the L*a*b* scale were taken for each specimen.

L* 100=perfect white

Chewing the Samples:

A mechanical instrument which was developed by Kleber et al. to simulate the human mastication of chewing gum, was used to treat the tooth specimens with the test chewing gum. For testing, a tooth specimen was placed both in the upper and lower tooth holders of the instrument. Then 15 ml of buffer was placed in the reservoir and warmed to 32 degrees C. by a thermostatically-controlled heating element. When the saliva reached the proper temperature, 2 cores (approximately 2 grams) of chewing gum were inserted between the repositioning paddles directly over the lower tooth specimen. Then the mastication motor was started and the two teeth were treated with the chewing gum for 20 minutes at a rate of 22 chewing cycles/minute. 8 teeth were used with gives 4 repetitions of the chewing. Each tooth was going through 5 cycles of 20 minutes.

Brushing Teeth:

Specimens were fastened and brushed for 1 minute with a normal toothbrush. There was an constant force on the brushing head of 150 g. The teeth was constant moisturised with a toothpaste slurry consisting of ⅓ toothpaste (FluoCalcin Classic) and ⅔ water. The brushing was done by hand and at a frequency of 60 brushing cycles/minute.

8 teeth were used and each tooth was brushed 2 times.

Measurements on the colour change was done before, between and after the 2 chewing periods.

Results

Stain Calculations:

% stain removal at $T_n = (E$ at $T_n/E$ max difference)*100

The overall change in the color of the stained teeth was calculated using the CIELAB equation $\Delta E=[(\Delta L^*)^2+(\Delta a^*)^2+(\Delta b^*)^2]^{1/2}$. The individual component L* (white) of the L*a*b* scale were also compared separately to determine the specific changes in the whiteness.

Data was tabulated using a spreadsheet program (Excel®, Microsoft), and analyzed by means of conventional statistics.

Statistical significance of data for each category was determined by using a 2-tail T-test p<0.05.

TABLE 5

Comparison of the whitening effect between tooth brush 2 * 1 minute and chewing gum 5 * 20 minutes. ΔE represents the overall colour change.

| Product | ΔE | ΔE$_{max}$ | % Reduction |
| --- | --- | --- | --- |
| TOOTHBRUSH | 3.98 ± 2.09$^a$ | 28.43 ± 4.26$^a$ | 13.80$^a$ |
| PLACEBO GUM B | 1.81 ± 0.51$^b$ | 28.39 ± 2.92$^a$ | 6.42$^b$ |
| GUM A | 4.47 ± 1.51$^a$ | 28.41 ± 3.49$^a$ | 16.35$^a$ |

% stain reduction = stain removal/total stain

Two-tailed T-Test: Values in the same column with the same letter are not statistically different, those with different letters are different at p<0.05.

Discussion & Conclusion

The total amount of stained removed from the specimens were significant better in the A chewing gum compared to the placebo gum with no active ingredients. Compared to the toothbrush the A gum also removes more stain, but not significant.

The comparison was made between 2*1 minute of tooth brushing and 5*20 min of chewing. These figures are chosen to simulate a realistic daily use of either toothbrush or chewing gum. It should be mentioned though that the chewing rate normally is 60 chew/min and the chewing machine only chews 22/min. This means a chewing time of only about 7 minutes.

Some 40 minutes chews were done in order to compensate for the slow chewing frequency. This was obvious though, that doubling the chewing time not provide the same effect as a faster chewing frequency. Therefore it will not be possible to compare our results to the results former achieved by C. Kleber where the chewing was done at another machine and at a frequency of about 50 cycles/minute.

The ΔE max values in table 5 are not significant different which implies that the amount of stain available for removal was the same in the different groups.

In general there are considerable deviations in the results. The reason for that is not clear but it could be due to the spectrophotometer even though it was calibrated at the beginning of each day and sometimes during the day. Never the less the measured values occasionally was decreased after chewing another 20 min.

The L* values represents as mentioned the white in colour and a perfect white is 100. The graph above shows the measured L* values and it is obvious that more and more stain is removed as the chewing time is prolonged in the A gum but not with the placebo gum B. This means that the chewing itself is not effective enough to remove the stain.

The change in colour between chewing was obvious to the eye. C. Kleber has mentioned that a ΔE around 1 can be detected by the human eye.

EXAMPLE 5

Study for Assessing Dental Plaque

The purpose of this human clinical study was to evaluate the potential for sugarless chewing gum containing zinc acetate to inhibit the formation of dental plaque on initially plaque-free tooth surfaces compared to conventional tooth brushing.

Study Design Summary

The test population consisted of 15 healthy adults who were known plaque-formers and regularly used chewing gum.

The clinical consisted of a randomized, double-blind, 3-way cross-over experimental design using a 2-day no-oral-hygiene plaque model. Adult subjects initially received a partial dental prophylaxis (no scaling or flossing) to remove all supragingival plaque. Then they were abstained for 2 days from all oral hygiene procedures other than the gum chewing or tooth brushing performed as a part of this study. Dental floss, toothpicks, mouthwashes, interdental stimulators, oral irrigation devices, and other commercial chewing gums and oral hygiene aids were not allowed during the trial periods. The 2-day no-oral-hygiene trial and 5-day washout periods occurred until all subjects had participated in each of the 3 treatment groups. The possibility of a carry-over effect from one test period to the next was minimized by requiring at least a 5-day washout period and by cleaning the participants' teeth before the start of each test period. In order to prevent a possible decrease in the plaque formation rates resulting from repeated dental cleanings, all plaque-free baselines were established by using rubber cup polishings with a standard dentifrice in lieu of a conventional dental prophylaxis with scaling and prophy paste. Also, no flossing was performed by the hygienists.

During each 2-day treatment period, the subjects assigned a chewing gum chewed 2 pieces of the gum for 10 minutes 5 times daily with no other oral hygiene. They also refrained from eating or drinking for 30 minutes after each chewing session in order to maximize the treatment effect. Those not assigned a gum brushed their teeth twice daily for 1 minute. After 2 days, each participant was checked for oral health and visually scored for plaque by an experienced dental examiner. The scoring occurred as close as possible to exactly 48 hours. Individual subjects were appointed and examined at the same time of day for each cross-over period. After the subjects had participated in each of the 3 cross-over periods, the plaque scores was tabulated and statistically compared by group. Furthermore, plaque data for the various tooth surfaces were separately analyzed in order to determine the dental areas where the chewing gum was most effective.

Baseline Examinations

Before the start of each of the 2-day test periods, the subjects had all supragingival plaque removed from their teeth by a dental hygienist, because a plaque-free baseline will increase the likelihood of detecting the activity of the zinc salt since it functions predominately by inhibiting the formation of new plaque on enamel surfaces. If sufficient plaque develops, however, the chewing gums may also function by mechanically removing some of the deposits. Thus, a plaque-free baseline will minimize the mechanical cleaning effect of the chewing gums and maximize the effect of the added zinc salt.

The dental cleaning consisted of only a rubber cup polishing with dentifrice in order to remove all visible plaque from the facial and lingual tooth surfaces. No scaling, flossing, or use of prophy paste was allowed to establish the plaque-free baselines. This procedure was followed because repeated complete dental prophylaxes over relatively short periods of time in cross-over studies may cause a decrease in plaque formation rates. If a subject required a complete dental prophylaxis to remove stain and calculus, this was performed at the screening exam before the start of the study.

Treatments

After removal of all plaque, the subject was assigned to one of 3 treatment groups according to a balanced Latin Square design. The 3 test groups consisted of 2 differently flavored chewing gums containing 0.5 mg zinc acetate compared to tooth brushing alone. The chewing gum and brushing treatments was unsupervised during the 2-day test periods. The subjects chewed 2 tablets of their assigned gum 5 times per day for 10 minutes each time. The chewing sessions occurred (1) after breakfast; (2) after lunch; (3) mid-afternoon at 3 p.m.; (4) after dinner; and (5) before bedtime. Timers were provided so that each subject could monitor their 10-minute chewing sessions. To maximize treatment substantivity and exposure time, subjects was refrained from eating or drinking for 30 minutes following each chewing session. The participants returned their unused gum so that usage levels and compliance can be estimated.

Test Products

The chewing gums under evaluation were provided by the sponsor in blank, coded packaging. The following products were tested:

(1) Flavored sugarless chewing gum no. 1 containing 0.50 mg zinc acetate per piece with no tooth brushing.
(2) Flavored sugarless chewing gum no. 2 containing 0.50 mg zinc acetate per piece with no toothbrushing
(3) Tooth brushing with no chewing gum (control).

The chewing gums used in this study was prepared in accordance with Good Manufacturing Procedures (GMP) at the sponsor's Food Approved, ISO Standardized facility. The gums contained NutraSweet® and the standard warning to phenylketonurics was on the packaging.

Final Examinations

The final exam for each subject was scheduled at exactly 48 hours following their baseline exam. Subjects continued to follow the same 48-hour sequence for each of the 3 cross-over periods in order to minimize any effect arising from the time of day that the chewing gum was last used. After each 2-day trial period, the subjects were scored first for oral health and then for dental plaque in order to determine the amount of plaque that formed on the teeth. All exams and cleanings were performed by experienced, licensed dental personnel using accepted methods of infection control in compliance with *OSHA's Standard for Occupational Exposure to Bloodborne Pathogens* (29 CRF 1910.1930) and *Indiana Public Law* (123-1988). Sterile instruments, disposable rubber gloves, and procedural masks were used for each exam in order to protect both the dental staff and subjects from trans-missible diseases.

The plaque was scored using the modified Quigley-Hein (MQH) plaque index. In order to facilitate scoring, the plaque was disclosed using a dye solution (Red Cote®, John O. Butler Company). Subjects rinsed with 5 ml of Red Cote® disclosant for 10 seconds, then expectorated and rinsed for 10 seconds with 10 ml of distilled water to remove the residual disclosant. Using a dental light and mouth mirror, the dental examiner visually scored the teeth for plaque deposits.

Scoring Methods

Oral Tissue Health

A visual inspection of the oral cavity using a standard dental light and mouth mirror were conducted at the screening and final examinations. The tissue structures checked included the buccal, labial and sublingual mucosa, gingivae, tongue, hard and soft palate, oropharynx, floor of the mouth, lips, and teeth. The site, size, and severity of any lesions or aberrations and tentative diagnosis, if possible, were recorded on the case report forms. A judgement were made as to whether or not the abnormalities were attributable to the test materials.

Modified Quigley-Hein (MQH) Plaque Index

Plaque deposits on the teeth were scored by an experienced examiner using the Quigley-Hein Index as modified by Turesky et al. (Turesky, S.; Gilmore, N. D.; and Glickman, I.: Reduced plaque formation by the chloromethyl analogue of Victamine C. *J Periodontol* 41:41-44, 1970.). It is a numerical index based on plaque area that gives greater attention to the gingival third of the tooth in order to differentiate relatively subtle amounts of plaque. In order to obtain greater sensitivity, plaque removal from the proximal as well as gingival areas were quanti-fled by dividing each tooth into six areas for scoring instead of just the two areas normally scored with the Turesky method (Deasy, M. J.; Singh, S. M.; Rustogi, K. N.; Petrone, D. M.; Battista, G.; Petrone, M. E.; and Volpe, A. R.: Effect of a dentifrice containing triclosan and a copolymer on plaque formation and gingivitis. *Clin Prev Dent* 13:12-19, 1991). Separate scores were measured for the marginal, mesial, and distal segments of both the facial and lingual surfaces of all teeth (except third molars) using the same criteria as the Turesky modification. The various surfaces of the teeth were assigned values as follows:

| | |
|---|---|
| 0 = | No visible plaque. |
| 1 = | Separate flecks of plaque at the cervical margin of the tooth. |
| 2 = | A thin, continuous band of plaque (up to 1 mm wide) at the cervical margin. |
| 3 = | A band of plaque wider than 1 mm but covering less than one-third of crown. |
| 4 = | Plaque covering at least one-third but less than two-thirds of crown. |
| 5 = | Plaque covering two-thirds or more of crown. |

An average plaque score per subject were calculated by summing the scores for all surfaces and dividing by the total number of surfaces scored.

Results

The results of the experiment clearly showed that for the subjects chewing a gum according to the present invention the formation of plaque was markedly reduced in comparison to the subject chewing the placebo gum. No side effects were observed during the study.

In the following other formulations of chewing gum are described. These formulations are also considered to be useful according to the present invention.

FORMULATION EXAMPLE 2

| Ingredients | % by weight |
| --- | --- |
| Gum base | 39.5 |
| Sorbitol | 39.99 |
| Glycerine | 5 |
| Green tea | 4 |
| Flavour | 2.7 |
| Craneberry | 2.7 |
| Dicalcium phosphate | 2.5 |
| Talc | 2.5 |
| Lecetin | 0.2 |
| Zinc | 0.5 |
| Acesulfane K | 0.2 |
| Aspartame | 0.2 |
| *Aloe vera* | 0.01 |

FORMULATION EXAMPLE 3

| Ingredients | % by weight |
| --- | --- |
| Gum base | 50 |
| Sorbitol | 34.98 |
| flavour | 3 |
| calcium carbonate | 4 |
| *eucalyptus* | 3 |
| xylitol | 4.6 |
| Acesulfane K | 0.2 |
| Aspartame | 0.2 |
| *Aloe vera* | 0.01 |
| Dicalcium phosphate | 0.01 |

FORMULATION EXAMPLE 4

| Ingredients | % by weight |
| --- | --- |
| Gum base | 45 |
| Sorbitol | 29.99 |
| xylitol | 10 |
| Maltitolsyrup | 5 |
| Glycerin | 2 |
| Flavour | 2 |
| *Aloe vera* | 1.5 |
| Baking soda | 1.5 |
| Champex | 1.5 |
| Black seaweed | 0.9 |
| Acesulfane K | 0.3 |
| Aspartame | 0.3 |
| Dicalcium phosphate | 0.01 |

FORMULATION EXAMPLE 5

| Ingredients | % by weight |
| --- | --- |
| Gum base | 39.5 |
| Sorbitol | 39.98 |
| Glycerine | 5 |
| Green tea extract | 3.9 |
| Flavour | 2.5 |
| Grape seed | 3 |
| Calcium carbonate | 3.5 |
| Talc | 1.5 |
| Lecetin | 0.2 |
| Zinc | 0.5 |
| Acesulfane K | 0.2 |
| Aspartame | 0.2 |
| Dicalcium phosphate | 0.01 |
| *Aloe vera* | 0.01 |

FORMULATION EXAMPLE 6

| Ingredients | % by weight |
| --- | --- |
| Gum base | 40 |
| Sorbitol | 30.31 |
| Maltitolsyrup | 5 |
| Lecithine | 0.2 |
| Green tea extract | 1.5 |
| *Aronia* | 2 |
| Zinc acetate | 0.06 |
| Sodium fluoride | 0.03 |
| NaHCO$_3$ | 1 |
| Calcium carbonate | 3 |
| Dicalcium phosphate | 3 |
| Calcium pyrophosphate | 6.7 |
| Titanium dioxide | 1 |
| Thyme | 0.5 |
| Acesulfame | 0.2 |
| Aspartame | 0.2 |
| Flavour | 1.3 |
| *Eucalyptus* | 1 |
| Xylitol | 5 |

FORMULATION EXAMPLE 7

| Ingredients | % by weight |
| --- | --- |
| Gum base | 40 |
| Sorbitol | 42.07 |
| Maltitolsyrup | 5 |
| Lecithine | 0.2 |
| Calcium carbonate | 4 |
| Sodium fluoride | 0.03 |
| *Aronia* | 3 |
| Green tea extract | 3 |
| Osteopontin | 0.5 |
| Vitamin C | 0.5 |
| Acesulfame | 0.2 |
| Aspartame | 0.2 |
| Flavour | 1.3 |

FORMULATION EXAMPLE 8

| Ingredients | % by weight |
| --- | --- |
| Gum base | 40 |
| Sorbitol | 44.37 |
| Maltitolsyrup | 5 |
| Lecithine | 0.2 |
| NaHCO3 | 1 |
| Sodium fluoride | 0.03 |
| *Aronia* | 3 |
| Green tea extract | 3 |
| Osteopontin | 0.5 |
| Vitamin C | 0.5 |
| Acesulfame | 0.2 |
| Aspartame | 0.2 |
| Flavour | 2 |

FORMULATION EXAMPLE 9

| Ingredients | % by weight |
| --- | --- |
| Gum base | 40 |
| Sorbitol | 37.17 |
| Maltitolsyrup | 5 |
| Lecithine | 0.2 |
| Calcium pyrophosphate | 7 |
| Sodium fluoride | 0.03 |
| *Aronia* | 3 |
| Green tea extract | 3 |
| Osteopontin | 0.5 |
| Vitamin C | 0.5 |
| Acesulfame | 0.3 |
| Aspartame | 0.3 |
| Flavour | 3 |

FORMULATION EXAMPLE 10

| Ingredients | % by weight |
| --- | --- |
| Gum base | 40 |
| Sorbitol | 33.97 |
| Maltitolsyrup | 5 |
| Calcium carbonate | 3 |
| Calcium pyrophosphate | 7 |
| Sodium fluoride | 0.03 |
| *Aronia* | 3 |
| Green tea extract | 3 |
| Osteopontin | 0.5 |
| Vitamin C | 0.5 |
| NaHCO3 | 1 |
| Acesulfame | 0.25 |
| Aspartame | 0.25 |
| Flavour | 2.5 |

FORMULATION EXAMPLE 11

| Ingredients | % by weight |
| --- | --- |
| Gum base | 40 |
| Sorbitol | 38.9 |
| Maltitolsyrup | 5 |
| Lecithine | 0.2 |
| Calcium carbonate | 4 |
| Dicalcium phosphate | 2.5 |
| Acesulfame | 0.2 |
| Aspartame | 0.2 |
| Flavour | 2 |
| *Aronia* | 3 |
| Green tea extract | 3 |
| Osteopontin | 0.5 |
| Vitamin C | 0.5 |

FORMULATION EXAMPLE 12

| Ingredients | % by weight |
| --- | --- |
| Gum base | 40 |
| Sorbitol | 37.17 |
| Maltitolsyrup | 5 |
| Lecithine | 0.2 |
| Calcium carbonate | 4 |
| Dicalcium phosphate | 2.5 |
| Acesulfame | 0.3 |
| Aspartame | 0.3 |
| Flavour | 3.5 |
| *Aronia* | 3 |
| Green tea extract | 3 |
| Osteopontin | 0.5 |
| Vitamin C | 0.5 |
| Sodium fluoride | 0.03 |

FORMULATION EXAMPLE 13

| Ingredients | % by weight |
| --- | --- |
| Gum base | 40 |
| Sorbitol | 33.37 |
| Maltitolsyrup | 5 |
| Lecithine | 0.2 |
| Acesulfame | 0.2 |
| Aspartame | 0.2 |
| Flavour | 2 |
| Green tea extract | 3 |
| Dicalcium phosphate | 2.5 |
| *Aronia* | 3 |
| Xylitol | 5 |
| Ig-lyt | 5 |
| Vitamin C | 0.5 |
| Sodium fluoride | 0.03 |

FORMULATION EXAMPLE 14

| Ingredients | % by weight |
| --- | --- |
| Gum base | 45 |
| Sorbitol | 41.17 |
| Maltitolsyrup | 5 |
| Acesulfame | 0.3 |
| Aspartame | 0.3 |

-continued

| Ingredients | % by weight |
|---|---|
| Flavour | 4 |
| Lecithine | 0.2 |
| NaHCO$_3$ | 1 |
| Sodium fluoride | 0.03 |
| Green tea extract | 2 |
| Osteopontin | 0.5 |
| Vitamin C | 0.5 |

FORMULATION EXAMPLE 15

| Ingredients | % by weight |
|---|---|
| Gum base | 45 |
| Sorbitol | 41.67 |
| Maltitolsyrup | 5 |
| Lecithine | 0.2 |
| Eucaluptus | 1.5 |
| NaHCO$_3$ | 0.03 |
| Zinc carbamate | 0.5 |
| Dicalciumphosphate | 3 |
| Osteopontin | 0.5 |
| Acesulfame | 0.2 |
| Aspartame | 0.2 |
| Flavour | 2.2 |

FORMULATION EXAMPLE 16

| Ingredients | % by weight |
|---|---|
| Gum base | 45 |
| Sorbitol | 32.57 |
| Maltitol syrup | 5 |
| Lecithine | 0.2 |
| Eucaluptus | 1.5 |
| NaHCO$_3$ | 0.03 |
| Zinc benzoate | 0.5 |
| dicalciumphosphate | 3 |
| Osteopontin | 0.5 |
| acesulfame | 0.3 |
| aspartame | 0.3 |
| Flavour | 2.6 |
| Green te extract | 2 |
| Thymol | 0.5 |
| Xylitol | 4 |
| Aronia | 2 |

It is within the standard procedures of a skilled person to adjust the level of the tooth brush cleaning effect according to needs, such as to increase the overall effect by increasing the amounts of active agents in general, such as by increasing the amounts of every active agent having tooth cleaning effect in a specific formulation by 10%, 20%, 50%, 75% or more of the actually stated amounts (and reduce the amount of filler or taste agents accordingly) or by adding additional active agents to the stated formulations (and reduce the amount of filler or taste agents accordingly). In case a particular effect, such as the anti-gingivitis effect, is to be enhanced the skilled person can increase the amounts of active agents providing that particular effect in a specific formulation by 10%, 20%, 50%, 75% or more of the actually stated amounts (and reduce the amount of filler or taste agents accordingly) or by adding at least one additional active agent providing that particular effect to the stated formulation (and reduce the amount of filler or taste agents accordingly). The same applies for the other active agents, such as anti-calculus agents. If the tooth cleaning effect is stronger than required, the skilled person can likewise minimize the amounts of active agents. The level or intensity of the tooth brush cleaning effect is thus adaptable according to requirements.

The various embodiments mentioned in the above description are non-limiting examples of the present invention. Other examples can be based by combination of the various figures, features and/or agents within the scope of the following claims.

The invention claimed is:

1. A method of avoiding abrasive cleaning damage to teeth side surfaces and gingiva during daily oral care, wherein the method comprises effectuating a daily oral care routine by performing the step of:
   providing a chewing gum in lieu of tooth brushing;
   the chewing gum being formed form a compressed mixture of granules and agents; and
   chewing the chewing gum in lieu of tooth brushing for at least 5 minutes per day in lieu of tooth brushing;
   wherein the chewing gum comprises at least two ingredients having at least two of the following effects: anti-plaque effect, anti-gingivitis effect, anti-calculus effect, or re-mineralization effect; and,
   wherein at least 55% of said at least two ingredients is released after 5 minutes of chewing when measured according to Ph. Eur. Version 5.0, January 2005, paragraph 2.9.25 (volume 1 page 260), and wherein said method further provides:
   a) a whitening effect which corresponds to at least 50% of the whitening effect of daily brushing of teeth with a new toothbrush,
   b) a fresh-breath effect which corresponds to at least 100% of the fresh-breath effect of daily brushing of teeth with a new toothbrush,
   c) an anti-plaque effect which corresponds to at as 60% of the anti-plaque effect of daily brushing of teeth with a new toothbrush,
   d) an anti-gingivitis effect which corresponds to at least 65% of the anti-gingivitis effect of daily brushing of teeth with a new toothbrush, and
   e) a re-mineralization effect which corresponds to at least 65% of the re-mineralization effect of daily brushing of teeth with a new toothbrush.

2. The method according to claim 1, wherein the chewing gum further comprises at least one ingredient comprising whitening agents and fresh-breath agents.

3. A method according to claim 2, wherein at least 30% of the said at least one ingredient is released after 5 minutes of chewing when measured according to Ph. Eur. Version 5.0, January 2005, paragraph 2.9.25 (volume 1 page 260).

4. A method according to claim 1, wherein the daily chewing of the chewing gum additionally provides:
   f) an anti-calculus effect which corresponds to at least 25% of the anti-calculus effect of daily brushing of teeth with a new toothbrush.

5. A method according to claim 1, wherein the daily chewing of the chewing gum provides a whitening effect which corresponds to at least 100% of the whitening effect of daily brushing of teeth with a new toothbrush.

6. A method according to claim 1, wherein the daily chewing of the chewing gum provides an anti-plaque effect which corresponds to at least 100% of the anti-plaque effect of daily brushing of teeth with a new toothbrush.

7. A method according to claim 1, wherein the daily chewing of the chewing gum provides an anti-gingivitis effect which corresponds to at least 100% of the anti-gingivitis effect of daily brushing of teeth with a new toothbrush.

8. A method according to claim 1, wherein the daily chewing of the chewing gum provides a re-mineralization effect which corresponds to at least 85% of the re-mineralization effect of daily brushing of teeth with a new toothbrush.

9. A method according to claim 1, wherein the daily chewing of the chewing gum provides an anti-calculus effect which corresponds to at least 85% of the anti-calculus effect of daily brushing of teeth with a new toothbrush.

10. A method according to claim 1, wherein the steps are repeated at least twice a day.

11. A method according to claim 10, wherein the steps are repeated in the morning and in the evening.

12. A method according to claim 10, wherein the steps are repeated after a meal.

13. A method according to claim 1, wherein the the chewing gum is a chewing gum tablet of a compressed mixture of gum base and ingredients of active agents, and optionally of other ingredients, and wherein the ingredients of active agents are selected from the group consisting of whitening agents, fresh-breath agents, ingredients having anti-plaque effect, anti-gingivitis effect, anti-calculus effect, or re-mineralization effect.

14. A method according to claim 13, wherein gum base granules are included in said mixture.

15. A method according to claim 13, wherein gum base granules are included in said mixture and ingredients of active agents are present in said gum base granules.

16. A method according to claim 14, wherein at least one fraction of said ingredients of active agents is present only in some of said gum base granules, and at least another fraction of said active agents is present only in others of said gum base granules.

17. A method according to claim 13, wherein the chewing gum is layered and different ingredients of active agents are present in the chewing gum in different layers.

18. A method according to claim 17, wherein at least one of the layers is substantially free of gum base.

19. A method according to claim 17, wherein one or more of said ingredients of active agents are present in the chewing gum in only one of the layers.

20. A method according to claim 17, wherein two or more of said ingredients of active agents are present in the chewing gum in different layers.

21. A method according to claim 17, wherein the chewing gum is coated.

22. A method according to claim 17, wherein at least one agent selected from the group consisting of fresh-breath agents, anti-gingivitis agents, anti-plaque agents, anti-calculus agents, and re-mineralization agents, is present in the coating.

23. A method according to claim 17, wherein the chewing gum comprises at least one barrier layer.

24. A method according to claim 17, wherein the gum base further includes at least one antibacterial agent.

* * * * *